United States Patent
Lowy et al.

(10) Patent No.: US 6,599,739 B1
(45) Date of Patent: Jul. 29, 2003

(54) INFECTIOUS PAPILLOMAVIRUS PSEUDOVIRAL PARTICLES

(75) Inventors: Douglas R. Lowy, Bethesda, MD (US); John T. Schiller, Silver Spring, MD (US); Richard B. Roden, Washington, DC (US)

(73) Assignee: The United States of America as represented by the Department of Health & Human Services, Washington, DC (US)

(*) Notice: Subject to any disclaimer, the term of this patent is extended or adjusted under 35 U.S.C. 154(b) by 0 days.

(21) Appl. No.: 09/509,748

(22) PCT Filed: Jul. 14, 1997

(86) PCT No.: PCT/US97/12115

§ 371 (c)(1), (2), (4) Date: Mar. 30, 2000

(87) PCT Pub. No.: WO98/02548

PCT Pub. Date: Jan. 22, 1998

Related U.S. Application Data

(60) Provisional application No. 60/022,104, filed on Jul. 17, 1996.

(51) Int. Cl.$^7$ .......................... C12N 15/00; C12N 15/63
(52) U.S. Cl. ..................... 435/325; 435/69.1; 435/91.4; 435/235.1; 435/320.1
(58) Field of Search .................... 435/235.1, 320.1, 435/456, 69.1, 325, 91.4; 424/204.1; 514/44

(56) References Cited

U.S. PATENT DOCUMENTS

| | | | |
|---|---|---|---|
| 5,437,951 A | 8/1995 | Lowy et al. | |
| 5,618,536 A | 4/1997 | Lowy et al. | |
| 5,709,996 A | 1/1998 | Lowy et al. | |
| 5,716,620 A | 2/1998 | Lowy et al. | |
| 5,744,142 A | 4/1998 | Lowy et al. | |
| 5,756,284 A | 5/1998 | Lowy et al. | |
| 5,855,891 A | 1/1999 | Lowy et al. | |
| 5,871,998 A | 2/1999 | Lowy et al. | |
| 5,985,610 A | 11/1999 | Lowy et al. | |
| 6,261,765 B1 * | 7/2001 | McCarthy et al. | 435/5 |

FOREIGN PATENT DOCUMENTS

| | | |
|---|---|---|
| WO | WO 96 11272 | 4/1996 |
| WO | WO 96 11274 A | 4/1996 |
| WO | WO 97 46693 | 12/1997 |

OTHER PUBLICATIONS

Roden et al., papillomavirus generation requires L1 and L2 capsid proteins and E2 transcription/replication protein, 1996, Journal of Investigative Dermatology, vol. 106, p. 912.*

R. Roden, et al., In vitro generation of infectious papillomaviruses requires a nonstructural viral protein in addition to the viral capsid proteins, 12$^{th}$ International Papillomavirus Conference, Jul. 23–28, 1995; Quebec City, Canada.

Androphy, E.J., et al. (1987) Bovine papillomavirus E2 trans–activating gene product binds to specific sites in papillomavirus DNA. Nature 325, 70–73.

Androphy, E.J., et al. (1985) Identification of the protein encoded by the E6 transforming gene of bovine papillomavirus. Science 230, 442–445.

Ascoli, C.A., et al. (1991) Identification of a novel nuclear domain. J. Cell Biol.112, 785–795.

Berglund, P., et al. (1993) Semliki forest virus expression system: production of conditionally infectious recombinant particles. Biotechnology 11, 916–920.

Berkner K.L. (1988) Development of Adenovirus vectors for the expression of heterologous genes. Biotechniques 6, 616–629.

Blitz, I.L., et al. (1991) The 68–Kilodalton E1 Protein of bovine papillomavirus is a DNA binding phosphoprotein which associates with the E2 transcriptional activator in vitro. J. Virol. 65, 649–656.

Boddy, M.N. (1996) PIC 1, a novel ubiquitin–like protein which interacts with the PML component of a multiprotein complex that is disrupted in acute promyelocytic leukaemia. Oncogen 13, 971–982.

Booy, F.P., et al. (1991) Liquid–crystalline, phage–like packing of encapsidated DNA in herpes simplex virus. Cell 64, 1007–1015.

Breitburd, F., et al.(1995) Immunization with viruslike particles from cottontial rabbit papillomavirus (CRPV) can protect against experimental CRPV infection. J. Virol. 69, 3959–3963.

Capecchi, M.R. (1980) High efficiency transformation by direct microinjection of DNA into cultured mammalian cells. Cell 22, 479–488.

Carrasco, L. (1997) The inhibition of cell functions after viral infection. FEBS Letters. 76, 11–15.

Carvalho, T., et al. (1995) Targeting of adenovirus E1A and E4–ORF3 proteins to nuclear matrix–associated PML bodies. J. Cell Biol. 131, 45–56.

(List continued on next page.)

Primary Examiner—Dave T. Nguyen
(74) Attorney, Agent, or Firm—Knobbe, Martens, Olson & Bear LLP

(57) ABSTRACT

The invention provides an infectious papillomavirus pseudoviral particle useful in gene transfer comprising: (a) a papillomavirus vector DNA which comprises an E2 binding site and an expression cassette comprising a gene and a sequence controlling expression of said gene; and (b) a papillomavirus capsid which comprises L1 and L2 structural proteins, such that said capsid encapsidates said vector DNA, wherein said gene is derived from a first biological species and said L1 structural protein is derived from a second biological species and said first biological species is different from said second biological species.

8 Claims, 1 Drawing Sheet

OTHER PUBLICATIONS

Chaney, W.G., et al. (1986) High–frequency transfection of CHO cells using polybrene. Somatic Cell Mol. Genet. 12, 237–244.

Chang, K.S., et al. (1995) The PML gene encodes a phosphoprotein associated with the nuclear matrix. Blood 85, 3646–3653.

Chelbi–Alix, M.K., et al. (1995) Induction of the PML protein by interferons in normal and APL cells. Leukemia 9, 2027–2033.

Cheng, G., et al. (1995) Divergent human papillomavirus type 16 variants are serologically cross–reactive. J. Infect. Dis. 172, 1584–1587.

Chiang, C.M., et al. (1992) Viral E1 and E2 proteins support replication of homologous and heterologous papillomavirus origins. Proc. Natl. Acad. Sci. USA 89, 5799–5803.

Christensen, N.D., et al. (1990) Antibody–mediated neutralization in vivo of infectious papillomaviruses. J. Virol. 64, 3151–3156.

Cowsert, L. M., et al. (1988) Identification of the bovine papillomavirus L1 gene product using monoclonal antibodies, Virology 165, 613–615.

Crystal, R.G. (1995) Transfer of genes to humans: early lessons and obstacles to success. Science 270, 404–410.

Day, P.M., et al. (1988) The papillomavirus minor capsid protein, L2, induces localization of the major capsid protein, L1, and the viral transcription/replication protein, E2, and PML oncogenic domains, J. Virol. 74, 142–150.

Desbois, C., et al. (1996) Exclusion of Int–6 from PML nuclear bodies by binding to the HTLV–I tax oncoprotein. Science 273, 951–953.

de The, H., et al. (1990) The t (15;17) translocation of acute promyelocytic leukemia fuses the retinoic acid receptor gene to a novel transcribed locus. Nature 347, 558–561.

Dick, J.E., et al. (1986) Genetic manipulation of hematopoeitic stem cells with retrovirus vectors. Trends Genet. 2, 165–170.

DiMaio, D. (1991) Transforming activity of boine and human papillomaviruses in cultured cells. Adv. Cancer Res. 56, 133–159.

Dollard, S.C., et al. (1992) Production of human papillomavirus and modulation of the infectious program in epithelial raft cultures. OFF. Genes Dev 6, 1131–42.

Doucas, V., et al. (1996) Adenovirus replication is coupled with the dynamic properties of the PML nuclear structure. Genes Dev. 10, 196–207.

Doyle, C., et al. (1985) Mutations in the cytoplasmic domain of the influenza virus hemagglutinin affect different stages of intracellular transport. J. Cell Biol. 100, 704–714.

Dyck, J. A., et al. (1994) A Novel macromolecular structure is a target of the promyelocyte–retinoic acid receptor oncoprotein. Cell 76, 333–343.

Dvoretzky, I., et al. (1980) A quantitative in vitro focus assay for bovine papilloma virus. Virology 103, 369–375.

Eglitis, M.A., et al. (1988) Retroviral vectors for introduction of genes into mammalian cells. Biotechniques 6, 608–614.

Elder, J.T., et al. (1981) Simian virus 40 as a eukaryotic cloning vehicle. Annu. Rev. Genet. 15, 295–340.

Epstein, A.L. (1984) Immunobiochemical characterization with monoclonal antibodies of Epstein–barr virus–associated early antigens in chemically induced cells. J. Virol. 50, 372–379.

Everett, R.D., et al. (1994) HSV–1 IE protein Vmw110 causes redistribution of PML. EMBO J. 13, 5062–5069.

Fagioli, et. al. (1994) Effect of the accute promyelocytic leukemia PML/RAR alpha protein on differentiation and survival of myeloid precursors. Leukemia, 8:S7–11.

Felgner, P.L., et al. (1989) Cationic liposome–mediated transfection. Focus 11(2), 21–25.

Fuerst, T.R., et al. (1986) Eukaryotic transient–expression system based on recombinant vaccinia virus that synthesizes bacteriophage T7 RNA polymerase. Proc. Natl. Acad. Sci. USA 83, 8122–8126.

Fuerst, T.R. et al. (1987) Use of a hybrid vaccinia virus–T7 RNA polymerase systems for expression of target genes. Mol. Cell. Biol. 7, 2538–2544.

Garry, R.F., et al. (1979) $Na^+$ and $K^+$ Concentrations and the regulation of protein synthesis in sindbis virus–infected chick cells. Virology 96, 108–120.

Gething, M. J., et al. (1981) Cell–surface expression of influenza haemagglutinin from a cloned DNA copy of the RNA gene. Nature 293, 620–625.

Gilboa, E., et al. (1986) Transfer and expression of cloned genes using retroviral vectors. Biotechniques 4, 504–512.

Grande, M.A., et al. (1996) PML–containing nuclear bodies: their spatial distribution in relation to other nuclear components. J. Cell. Biochem 63, 280–291.

Grignani, F., et al. (1995) Promyelocytic leukemia–specific PML–retinoic acid α receptor fusion protein interferes with erythroid differentiation of human drythroleukemia K562 cells. Cancer Res. 55: 440–443.

Grignani, F., et al. (1996) Effects on differentiation by the promyelocytic leukemia PML/RARα protein depend on the fusion of the PML protein dimerization and RARα DNA binding domains. EMBO J. 15, 4949–4958.

Grotzinger, T., et al. (1996) A highly amplified mouse gene is homologous to the human interferon–responsive Sp100 gene encoding an autoantigen associated with nuclear dots. Mol. Cell. Biology 16, 1150–1156.

Hagensee, M.E., et al. (1993) Growing human papillomaviruses and virus–like particles in the laboratory. Papillomavirus Report 4, 121–124.

Hagensee, M.E., et al. (1993) Self–assembly of human papillomavirus type 1 capsids by expression of the L1 protein alone or by coexpression of the L1 and L2 capsid proteins. J. Virol. 67, 315–322.

Heino, P., et al. (1995) Human papillomavirus type 16 capsid proteins produced from recombinant semliki forest virus assemble into virus–like particles. Virology 214, 349–359.

Hirt, B. (1967) Selective extraction of polyoma DNA from infected mouse cell cultures. J.Mol.Biol. 26, 365–369.

Hubbert, N.L., et al. (1988) Bovine papilloma virus–transformed cells contain multiple E2 proteins. Proc. Natl. Acad. Sci. USA 85, 5864–5868.

Ishov, A.M., et al. (1996) The periphery of nuclear domain 10 (ND10) as site of DNA virus deposition. J. Cell. Biol. 134, 815–826.

Jiang, W.Q., et al. (1996) Intranuclear redistribution of SV40T, p53, and PML in a conditionally SV40T–Immortalized cell line. Exp. Cell. Res. 229, 289–300.

Jin, X. W., et al. (1989) Identification of L2 open reading frame gene products of bovine papillomovirus type 1 using monoclonal antibodies. J.Gen.Virol. 70, 1133–1140.

Kakizuka, A., et al. (1991) Chromosomal translocation t(15;17) in human acute promyelocytic leukemia fuses RARα with a novel putative transcription factor, PML. Cell 66, 663–674.

Karlsson, S., et al. (1986) Stable gene transfer and tissue–specific expression of a human globin gene using adenoviral vectors. EMBO J. 5, 2377–2385.

Kawai, S., et al. (1984) New procedure for DNA transfection with polycation and dimethyl sulfoxide. Mol. Cell. Biol. 4, 1172–1174.

Kirnbauer, R., et al. (1993) Efficient self–assembly of human papillomavirus type 16 L1 and L1–L2 into virus–like particles. J. Virol. 67(12), 6929–36.

Kirnbauer, R., et al. (1992) Papillomavirus L1 major capsid protein self–assemblies into virus–like particles that are highly immunogenic. Proc. Natl. Acad. Sci. USA 89, 12180–12184.

Kreider, J.W., et al. (1987) Laboratory production in vivo of infectious human papillomavirus type 11. J. Virol. 61(2), 590–593.

Lambert, P.F., et al. (1989) Genetic assignment of multiple E2 gene products in bovine papillomavirus–transformed cells. J. Virol. 63, 3151–3154.

Lambert, P.F., et al. (1989) Functional analysis of the papillomavirus E2 trans–activator in Saccharomyces cerevisiae. Genes Dev. 3, 38–48.

Lamond, A.I., et al. (1993) The coiled body. Trends in Cell.Biol. 3, 198–204.

Lavau, C., et al. (1995) The acute promyelocytic leukaemia–associated PML gene is induced by interferon. Oncogene 11, 871–876.

Law, M.F., et al. (1981) Mouse cells transformed by bovine papillomavirus contain only extrachromosomal viral DNA sequences. Proc Natl. Acad. Sci. USA 78, 2727–2731.

Li, R., et al. (1989) Specific recognition nucleotides and their DNA context determine the affinity of E2 protein for 17 binding sites in the BPV–1 genome. Genes Dev. 3, 510–526.

Lilejeström, P., et al. (1991) A new generation of animal cell expresssion vectors based on the semliki forest virus replicon. Biotechnology 9, 1356–1361.

Luckow, V.A., et al. (1988) Trends in the development of baculovirus expression vectors. Biotechnology, 6, 47–55.

Mackett, M., et al. (1985) *DNA cloning: A Practical Approach*, D.M. Glover, ed., IRL Press, Oxford, vol. 2, p. 191–211.

Mallon, R.G., et al. (1987) DNA–binding activity of papillomavirus proteins. J. Virol. 61, 1655–1660.

Mannino, R.J., et al. (1988) Liposome mediated gene transfer. Biotechniques 6, 683–690.

Mansour, S.L., et al. (1985) An adenovirus vector system used to express polyoma virus tumor antigens. Proc. Natl. Acad. Sci. USA 82, 1359–1363.

Maul, G.G., et al. (1996) Nuclear domain 10 as preexisting potential replication start sites of herpes simplex virus type–1. Virology 217, 67–75.

Mauer, R. (1989) Cationic liposome–mediated transfection of primary cultures of rat pituitary cells. Bethesda Res. Lab. Focus 11, 25–27.

McBride, A.A., et al. (1991) The papillomavirus E2 regulatory proteins. J. Biol. Chem. 266, 18411–18414.

Meyers, et al. (1992) Biosynthesis of human papillomavirus from a continuous cell line upon epithelial differentiation. Science 257, 971–973.

Mohr, I.J., et al. (1990) Targeting the E1 replication protein to the papillomavirus origin of replication by complex formation with the E2 transactivator. Science 250, 1694–1699.

Monini, P., et al. (1993) Cooperative DNA binding of the bovine papillomavirus E2 transcriptional activator is antagonized by truncated E2 polypeptides. J. Virol. 67, 5668–5676.

Morrissey, L.C., et al. (1989) Trans activation by the bovine papillomavirus E2 protein in saccharomyces cerevisiae. J. Virol. 63, 4422–4425.

Moss, B. (1985) *Viroloyg*, B.N. Fields, et al., eds., Raven Press, New York, p. 685–703.

Muller, M., et al. (1995) Papillomavirus capsid binding and uptake by cells from different tissues and species. J. Virol 69(2), 948–954.

Mulligan, R.C. (1993) The basic science of gene therapy. Science 260, 926–932.

Neumann, E., et al. (1982) Gene transfer into mouse lyoma cells by electroporation in high electric fields. EMBO J. 1, 841–845.

Oppenheim, A., et al. (1992) a cis–acting DNA signal for encapsidation of simian virus 40. J. Virol. 66, 5320–5328.

Puvion–Dutilleul, F., et al. (1995) Adenovirus infection induces rearrangements in the intranuclear distribution of the nuclear body–associated PML protein. Exp. Cell Res. 218, 9–16.

Rassoulzadegan, M., et al. (1982) High frequency of gene transfer after fusion between bacteria and eukaryotic cells. Nature 295, 257–259.

Rigby, P.W.J. (1982) *Genetic Engineering*, R. Willianson, ed., Academic Press, London, vol. 3, p. 83–141.

Rigby, P.W.J. (1983) Cloning vectors derived from animal viruses. J Gen. Virol. 64, 255–266.

Robbins, J.B., et al. (1995) Perspective: Hypothesis: Serum IgG antibody is sufficient to confer protection against infectious diseases by inactivating the inoculum. J. Infect. Dis. 171, 1387–1398.

Roden, R.B.S., et al. (1994) Neutralization of bovine papillomavirus by antibodies to L1 to L2 capsid proteins. J. Virol. 68, 7570–7574.

Roden, R.B.S., et al. (1994) Interaction of papillomaviruse with the cell surface. J. Virol. 68(11), 7260–7266.

Roden, R.B.S., et al. (1995) Papillomavirus L1 capsids agglutinate mouse erythrocytes through a proteinaceous receptor, J. Virol. 69, 5147–5151.

Roden, R.B.S., et al. (1996) In vitro generation and type–specific neutralization of a human papillomavirus type 16 virion pseudotype. J. Virol. 70, 5875–5883.

Roden, R.B.S., et al. (1996) Papillomavirus generation requires L1 and L2 capsid proteins and e2 transcription/replication protein. J Invest. Derm. 106, 912. Abstract 641.

Rose, R.C., et al. (1994) Serological differentiation of human papillomavirus types 11, 16, and 18 using recombinant virus–like particles. J. Gen Virol. 75, 2445–2449.

Sambrook, J., et al. (1986) Expression of human tissue–type plasminogen activator from lytic viral vectors and in established cell lines. Mol Biol. Med 3, 459–481.

Sarver, N. et al. (1982) Transformation and replication in mouse cells of a bovine papillomavirus–pML2 plasmid vector that can be rescued in bacteria. Proc. Natl. Acad. Sci. USA 79, 7147–7151.

Sasagawa, et al. (1995) Synthesis and assembly of virus–like particles of human papillomavirus type 6 and type 16 in fission yeast Schixosaccharomyces pombe. Virology 206(1), 126–135.

Schaffner, W. (1980) Direct transfer of cloned genes from bacteria to mammalian cells. Proc. Natl. Sci. USA 77, 2163.

Seedorf, K., et al. (1985) Human papillomavirus type 16 DNA sequence. Virology 145, 181–185.

Solnick, D. (1981) Construction of an adenovirus–SV40 recombinant sv40 T antigen from an adenovirus late promoter. Cell 24, 135–143.

Spalholz, B.A., et al. (1985) Transactivation of a bovine papilloma virus transcriptional regulatory element by the E2 gene product. Cell 42, 183–191.

Stenlund, A., et al. (1985) Messenger RNAs from the transforming region of bovine papilloma virus type I. J. Mol. Biol. 182, 541–554.

Strauss, J.H., et al. (1994) The alphaviruses: gene expression, replication, and evolution. Micro. Rev. 58, 491–562.

Stuurman, N., et al. (1992) A monoclonal antibody recognizing nuclear matrix–associated nuclear bodies. J. Cell. Science 101, 773–784.

Summers, M.D., et al. (1987) A manual of methods for baculovirus vectors and insect cell culture procedures. Texas Agricultural Experiment Station, College Station Texas., Bulletin No. 1555.

Sun, S., et al. (1990) Identification of a 68–kilodation nuclear ATP–binding phosphoprotein enclosed by bovine papillomavirus type 1. J. Virol. 64, 5093–5105.

Sundberg, J.P. (1987) Papillomavirus infection in animals. (K. Syrjanen, et al. Eds.), pp. 41–103. Springer–Verlag, Berlin.

Suzich, J.A., et al. (1995) Systemic immunication with papillomavirus L1 protein completely prevents the development of viral mucosal papillomas. Proc. Natl. Sci. USA 92, 11553–11557.

Szostecki, D. et al. (1990) Isolation and characterization of cDNA encoding a human nuclear antigen predominantly recognized by autoantibodies from patients with primary biliary cirrhosis. J. Immunol. 145, 4338–4347.

Thummel, C., et al. (1981) Expression of SV40 T antigen under control of adenovirus promoters. Cell 23, 825–836.

Thummel, C., et al. (1982) Construction of adenovirus expression vectors by site–directed in vivo recombination. J. Mol. Appl. Genet. 1, 435–446.

Thummel, C., et al. (1983) Translational control of SV40 T antigen expressed from the adenovirus late promoter. Cell 33, 455–464.

Turek, L.P. (1994) The structure, function, and regulation of papillomaviral genes in infection and cervical cancer. Adv. Virus Res. 44, 305–356.

Ustav, M., et al. (1991) Transient replication of BPV–1 requires two viral polypeptides enclosed by the E1 and E2 open reading frames. EMBO J. 10, 449–457.

Volpers, C., et al. (1995) Binding and internalization of human papillomavirus type 33 virus–like particles by eukaryotic cells. J. Virol. 69, 3258–3264.

Wilson, V.G., et al. (1991) A bovine papillomavirus E1–related protein binds specifically to bovine papillomavirus DNA. J. Virol. 65, 5314–5322.

Wolff, J.A., et al. (1990) Direct gene transfer into mouse muscle in vivo. Science 247, 1465–1468.

Yang, N.S. et al. (1990) In Vivo and in vitro gene transfer to mammalian somatic cells by particel bombardment. Proc. Natl. Acad. Sci. USA 87, 9568–9572.

Zhang, Y–L., et al. (1987) Levels of bovine papillomavirus RNA and protein expression correlate with variations in the tumorigenic phenotype of hamster cells. J. Virol. 61, 2924–2928.

Zhou, J., et al. (1993) Synthesis and assembly of infectious bovine papillomavirus particles in vitro. J Gen Virol. 74, 763–768.

Zhou, J., et al. (1991) Expression of vaccinia recombinant HPV 16 L1 and L2 ORF proteins in epithelial cells is sufficient for assembly of HPV virion–like particles. Virology 185, 251–257.

Zhou, J., et al. (1994) Interaction of human papillomavirus (HPV) type 16 capsid proteins with HPV DNA requires an intact L2 N–terminal sequence. J. Virol. 68, 619–625.

Zimmermann, U. (1982) Electric field–mediated fusion and related electrical phenomena. Biochem. Biophys. Acta. 694, 227–277.

zur Hausen, H., et al. (1994) Human papillomaviruses. Ann. Rev. Microbiol. 48, 427–447.

* cited by examiner

SEQUENCE LISTING

```
<160> NUMBER OF SEQ ID NOS: 12

<210> SEQ ID NO 1
<211> LENGTH: 52
<212> TYPE: DNA
<213> ORGANISM: Artificial Sequence
<220> FEATURE:
<223> OTHER INFORMATION: PCR Primer

<400> SEQUENCE: 1
ccgctggatc ccactattat atagcaccat ggcgttgtgg caacaaggcc ag            52

<210> SEQ ID NO 2
<211> LENGTH: 21
<212> TYPE: DNA
<213> ORGANISM: Artificial Sequence
<220> FEATURE:
<223> OTHER INFORMATION: PCR Primer
```

-continued

```
<400> SEQUENCE: 2
cagttgagac tagagagcca c                                              21

<210> SEQ ID NO 3
<211> LENGTH: 21
<212> TYPE: DNA
<213> ORGANISM: Artificial Sequence
<220> FEATURE:
<223> OTHER INFORMATION: PCR Primer

<400> SEQUENCE: 3
gtggctctct agtctcaact g                                              21

<210> SEQ ID NO 4
<211> LENGTH: 55
<212> TYPE: DNA
<213> ORGANISM: Artificial Sequence
<220> FEATURE:
<223> OTHER INFORMATION: PCR Primer

<400> SEQUENCE: 4
gcggtggatc cttatttttt tttttttttt gcaggcttac tggaagtttt ttggc         55

<210> SEQ ID NO 5
<211> LENGTH: 47
<212> TYPE: DNA
<213> ORGANISM: Artificial Sequence
<220> FEATURE:
<223> OTHER INFORMATION: PCR Primer

<400> SEQUENCE: 5
gcggtagatc taatatgagt gcacgaaaaa gagtaaaacg tgccagt                  47

<210> SEQ ID NO 6
<211> LENGTH: 47
<212> TYPE: DNA
<213> ORGANISM: Artificial Sequence
<220> FEATURE:
<223> OTHER INFORMATION: PCR Primer

<400> SEQUENCE: 6
ccgctagatc tagggagata cagcttctgg ccttgttgcc acaacgc                  47

<210> SEQ ID NO 7
<211> LENGTH: 37
<212> TYPE: DNA
<213> ORGANISM: Artificial Sequence
<220> FEATURE:
<223> OTHER INFORMATION: PCR Primer

<400> SEQUENCE: 7
ccgctggatc cgcaccatgg caaacgataa aggtagc                             37

<210> SEQ ID NO 8
<211> LENGTH: 32
<212> TYPE: DNA
<213> ORGANISM: Artificial Sequence
<220> FEATURE:
<223> OTHER INFORMATION: PCR Primer

<400> SEQUENCE: 8
gcggtggatc cgatcttgca acttatcact ac                                  32

<210> SEQ ID NO 9
<211> LENGTH: 36
```

```
<212> TYPE: DNA
<213> ORGANISM: Artificial Sequence
<220> FEATURE:
<223> OTHER INFORMATION: PCR Primer

<400> SEQUENCE: 9
ccgctggatc cgcaccatgg agacagcatg cgaacg                                36

<210> SEQ ID NO 10
<211> LENGTH: 32
<212> TYPE: DNA
<213> ORGANISM: Artificial Sequence
<220> FEATURE:
<223> OTHER INFORMATION: PCR Primer

<400> SEQUENCE: 10
gcggtggatc cgaagaaaag gcaatggcag tg                                    32

<210> SEQ ID NO 11
<211> LENGTH: 30
<212> TYPE: DNA
<213> ORGANISM: Artificial Sequence
<220> FEATURE:
<223> OTHER INFORMATION: PCR Primer

<400> SEQUENCE: 11
cggcaagctt gcaatgtgct gtgtcagttg                                       30

<210> SEQ ID NO 12
<211> LENGTH: 30
<212> TYPE: DNA
<213> ORGANISM: Artificial Sequence
<220> FEATURE:
<223> OTHER INFORMATION: PCR Primer

<400> SEQUENCE: 12
cgcgaagctt aacggtgatg gtgtgattat                                       30
```

INFECTIOUS PAPILLOMAVIRUS PSEUDOVIRAL PARTICLES

RELATED APPLICATIONS

This application is a filing under 35 U.S.C. §371 of International Application No. PCT/US97/12115, filed Jul. 14, 1997, which claims the benefit of priority of U.S. Application No. 60/022,104, filed Jul. 17, 1996.

FIELD OF THE INVENTION

The field of the invention is related to infectious papillomavirus pseudoviral particles useful in gene transfer.

BACKGROUND OF THE INVENTION

Gene transfer is a laboratory strategy in which the genetic repertoire of eukaryotic cells is modified. Essentially, gene transfer involves the delivery, to target cells, of an expression cassette made up of one or more genes and the sequences controlling their expression. The transfer process is accomplished by delivery of the cassette to the cell where it can function appropriately.

Considerable effort has been made to develop delivery systems to express foreign proteins in eukaryotic cells. These systems can be divided into two types: transfection and infection.

The first type of delivery system for introducing cloned DNAs into eukaryotic cells involves transfection. Calcium phosphate- or DEAE-dextran-mediated transfection is the most widely used method. The polycation Polybrene allows the efficient and stable introduction of plasmid DNAs into cultured cells that are relatively resistant to transfection by other methods (Kawai, S., and Nishizawa, M., 1984, Mol. Cell. Biol. 4, 1172; Chaney, W. G., et al., 1986, Somatic Cell Mol. Genet. 12, 237). In protoplast fusion, protoplasts derived from bacteria carrying high numbers of copies of a plasmid of interest are mixed directly with cultured mammalian cells, and fusion of the cell membranes is accomplished with polyethylene glycol, with the result that the contents of the bacteria are delivered into the mammalian cells (Schaffner, W., 1980, Proc. Natl. Acad. Sci. USA 77, 2163; Rassoulzadegan, M., et al. 1982, Nature 295, 257). Electroporation features the application of electric pulses to mammalian and plant cells so that DNA is taken directly into the cell cytoplasm (Neumann, E., et al., 1982, EMBO J. 1, 841; Zimmermann, U., 1982, Biochim. Biophys. Acta 694, 227). Artificial membrane vesicles, such as liposomes and cationic lipids, are useful as delivery vehicles in vitro and in vivo (Mannino, R. J., and Gould-Fogerite, S., 1988, BioTechniques 6, 682; Felgner, P. L., and Holm, M., 1989, Bethesda Res. Lab. Focus 11, 21; Maurer, R. A., 1989, Bethesda Res. Lab. Focus 11, 25). Direct microinjection into nuclei is effective, but it cannot be used to introduce DNA on a large scale (Capecchi, M. R., 1980, Cell 22, 479). Finally, naked DNA can, by itself, be placed into cells by particle bombardment (Yang, N. S., et al., 1990, Proc. Natl. Acad. Sci. USA 87, 9568), or taken up by cells, particularly when injected into muscle (Wolff, J. A., et al., 1990, Science 247, 14651).

The other type of delivery system is mediated by infection and involves the use of viral expression vectors derived from simian virus 40 (SV40) (Elder, J. T., et al., 1981, Annu. Rev. Genet. 15, 295; Gething, M. J., and Sambrook, J., 1981, Nature 293, 620; Rigby, P. W. J., 1982, *Genetic engineering*, R. Williamson, ed., Academic Press, London, vol. 3, p. 83; Rigby, P. W. J., 1983, J. Gen. Virol. 64, 255; Doyle, C., et al., 1985, J. Cell. Biol. 100, 704; Sambrook, J., et al., 1986, Mol. Biol. Med. 3, 459), vaccinia virus (Mackett, M., et al., 1985, *DNA cloning: A practical approach*, D. M. Glover, ed., IRL Press, Oxford, vol. 2, p. 191; Moss, B., 1985, *Virology*, B. N. Fields, et al., eds., Raven Press, New York, p. 685; Fuerst, T. R., et al., 1986, Proc. Natl. Acad. Sci. USA, 83, 8122; Fuerst, T. R., et al., 1987, Mol. Cell. Biol. 7, 2538), adenovirus (Solnick, D., 1981, Cell 24, 135; Thummel, C., et al., 1981, Cell 23, 825; Thummel, C., et al., 1982, J. Mol. Appl. Genet. 1, 435; Thummel, C, et al., 1983, Cell 33, 455; Mansour, S. L., et al., 1985, Proc. Natl. Acad. Sci. USA 82, 1359; Karlsson, S., et al., 1986, EMBO J. 5, 2377; Berkner, K. L., 1988, BioTechniques 6, 616), retroviruses (Dick, J. E., et al., 1986, Trends Genet. 2, 165; Gilboa, E., et al., 1986, BioTechniques 4, 504; Eglitis, M. A., and Anderson, W. F., 1988, BioTechniques 6, 608), and baculoviruuses (Luckow, V. A., and Summers, M. D., 1988, Bio/Technology 6, 47).

Expression of proteins from cloned genes in eukaryotic cells has been used for a number of different purposes: to confirm the identity of a cloned gene by using immunological or functional assays to detect the encoded protein, to express genes encoding proteins that require posttranslational modifications such as glycosylation or proteolytic processing, to produce large amounts of proteins of biological interest that are normally available in only limited quantity from natural sources, to study the biosynthesis and intracellular transport of proteins following their expression in various cell types, to elucidate structure-function relationships by analyzing the properties of normal and mutant proteins, to express intron-containing genomic sequences that cannot be transcribed correctly into mRNA in prokaryotes, and to identify DNA sequence elements involved in gene expression. Because expression of proteins can serve so many different purposes, there is a need for new delivery systems to meet the challenge of getting foreign DNA into eukaryotic cells. The invention satisfies this need.

These and other objects of the invention will be apparent to one of ordinary skill in the art upon consideration of the specification as a whole.

SUMMARY OF THE INVENTION

In one aspect, the invention provides an infectious papillomavirus pseudoviral particle.

In another aspect, the invention provides a HPV16{BPV1} virion.

In still another aspect, the invention provides an infectious papillomavirus pseudoviral particle comprising: a papillomavirus vector DNA which comprises an E2 binding site and an expression cassette comprising a gene and a sequence controlling expression of the gene; and a papillomavirus capsid which comprises L1 and L2 structural proteins, such that the capsid encapsidates the vector DNA, where the gene is derived from a first biological species and the L1 structural protein is derived from a second biological species and the first biological species is different from the second biological species.

In yet another aspect, the invention provides the here-described infectious papillomavirus pseudoviral particle, where the first biological species is BPV1 and the second biological species is HPV16.

In a different embodiment, the invention relates to a method of making infectious papillomavirus pseudoviral particles comprising: providing a cell line which expresses papillomavirus E2 DNA binding protein and L1 and L2 structural proteins; transforming the cell line with a papillomavirus vector DNA which comprises an E2 binding site and an expression cassette comprising a gene and a sequence controlling expression of the gene, where the papillomavirus E2 binding site is a cognate binding site of the E2 DNA binding protein, and where the gene is derived from a first biological species and the L1 structural protein is derived from a second biological species and the first biological species is different from the second biological species; providing conditions for the encapsidation of the vector DNA by a capsid which comprises the L1 and L2 structural proteins to generate the particles; and harvesting the particles.

In the above method, the cell line may be a mammalian cell line, an insect cell line, or a yeast cell line.

In yet a different embodiment, the invention relates to a cell line comprising the here-described infectious papillomavirus pseudoviral particle.

In still a different embodiment, the invention relates to a method of transferring a gene into a cultured mammalian cell comprising: providing the here-described infectious papillomavirus pseudoviral particle; and infecting a cultured mammalian cell with the particle such that the cultured mammalian cell is transformed with the gene.

In another manifestation, the invention provides a method of screening for infectious papillomavirus pseudoviral particles comprising administering test particles to cultured mammalian cells capable of being infected thereby and scoring for infectivity thereof.

In a further manifestation, the invention provides a composition comprising the here-described infectious papillomavirus pseudoviral particle, where the gene in the expression cassette encodes a product capable of having a therapeutic effect when administered in a therapeutically effective amount to a host subject in need thereof.

In an additional manifestation, the invention provides a composition comprising the here-described infectious papillomavirus pseudoviral particle, where the gene in the expression cassette encodes a product capable of having an immunogenic effect when administered in an immunogenically effective amount to a host subject in need thereof.

The invention also relates to a method of providing a human with an immunogenic protein comprising: infecting cells of the human in vivo with the here-described infectious papiliomavirus pseudoviral particle, where the gene in the expression cassette encodes the immunogenic protein, the cells expressing an immunogenically effective amount of the immunogenic protein.

The invention further relates to a method of providing a human with a therapeutic protein comprising: infecting cells of the human in vivo with the here-described infectious papillomavirus pseudoviral particle, where the gene in the expression cassette encodes the therapeutic protein, the cells expressing a therapeutically effective amount of the therapeutic protein.

In this method, the cells may be epithelial cells, and the therapeutic protein may have a systemic effect. Or the therapeutic protein may have a local effect on the epithelial cells. Or the therapeutic protein may be Factor IX and the expression of the therapeutic protein may result in treatment of hemophilia. Or the therapeutic protein may be herpes simplex virus thymidine kinase and the expression of the therapeutic protein may result in treatment of skin cancer.

This method may involve serial administration of different serotypes and thus comprise infecting cells of the human in vivo with a second infectious papillomavirus pseudoviral particle where the second infectious papillomavirus pseudoviral particle differs from the first infectious papillomavirus pseudoviral particle in that the second is a different serotype from the first.

The invention additionally relates to an infectious papillomavirus pseudoviral particle comprising a papillomavirus genome, which comprises an E2 binding site and an expression cassette comprising a gene and a sequence controlling expression of the gene, and a papillomavirus capsid, which comprises L1 and L2 structural proteins, such that the capsid encapsidates the genome, where the E2 binding site is derived from a first papillomavirus serotype and the L1 structural protein is derived from a second papillomavirus serotype and the first papillomavirus serotype is different from the second papillomavirus serotype.

The invention moreover relates to a method of making infectious virus pseudoviral virions in nonmammalian cells comprising: providing a nonmammalian cell line which expresses the nonstructural protein(s) of the virus for packaging the viral genome of the virus in the empty capsid of the virus, and which expresses the structural proteins of the virus capsid; transforming the cell line with the viral genome which comprises the packaging signal, and which further comprises an expression cassette comprising a gene and a sequence controlling expression of the gene, and where the gene is derived from a first biological species and the viral capsid is derived from a second biological species and the first biological species is different from the second biological species; providing conditions for the encapsidation of the viral genome by the viral capsid to generate the virions; and harvesting the virions.

DETAILED OF THE PREFERRED EMBODIMENT

Figure 1:
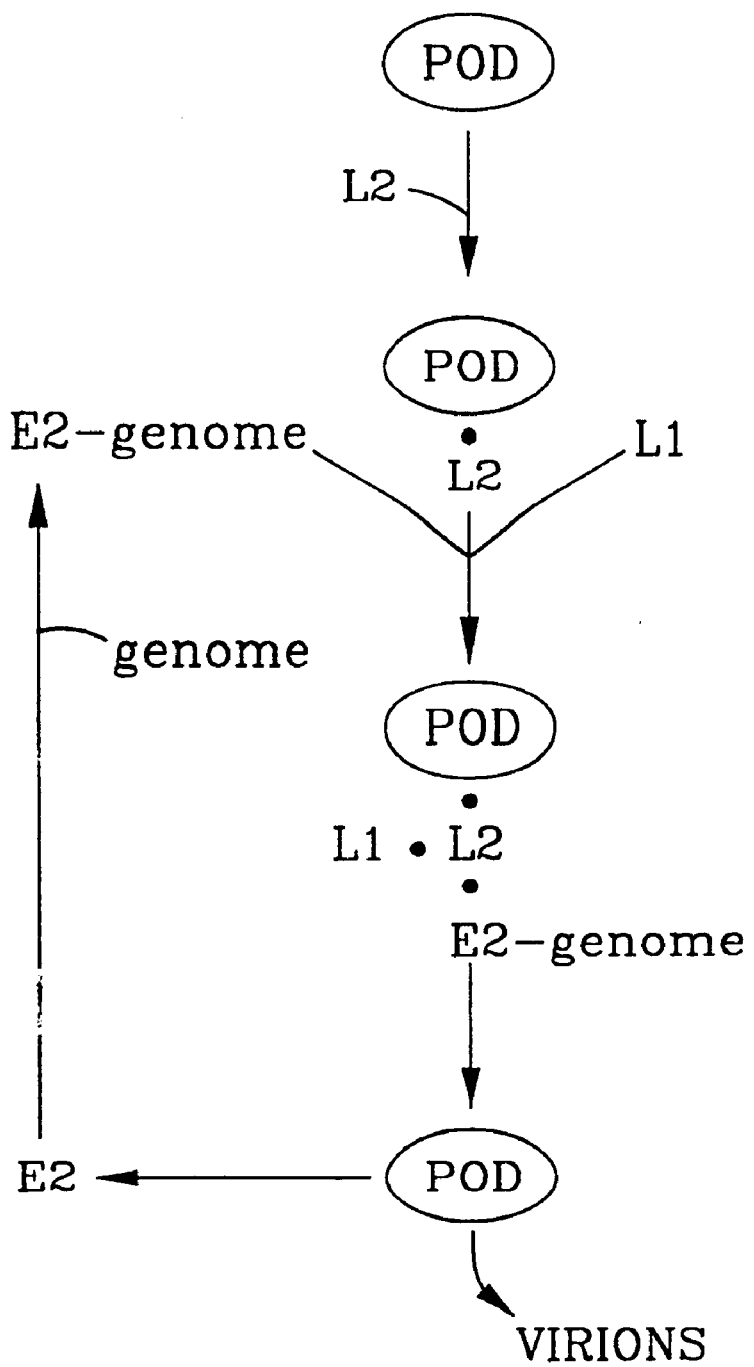
FIG. 1. A model for L2-mediated assembly of papillomavirus virions. This model is discussed at length in the text. Briefly, it is proposed that L2 acts to mediate papillomavirus assembly by causing the concentration of the virion components within the PODs. L2 will localize in the PODs independently of other viral proteins. The L2 localization will cause the subsequent recruitment of E2 with the bound genome and L1. These events are independent of each other. This L2-L1-E2-genome association within the PODs confers an appropriate environment and/or concentration for virion assembly.

The invention satisfies the need for new delivery systems to meet the challenge of getting cloned DNA into eukaryotic cells by providing infectious papillomavirus pseudoviral particles. Section I describes in vitro generation of infectious BPV virions and infectious HPV16{BPV1} pseudoviral particles in mammalian cells. Section II elaborates the requirements for the papillomavirus capsid proteins, the viral transcription/replication protein, E2, and POD nuclear structures for encapsidation. Section III details the in vitro generation of infectious BPV virions in nonmammalian cells. Section IV describes the use of infectious papillomavirus pseudoviral particles in a specialized case of gene transfer, that of gene therapy and gene immunization.

1. In Vitro Generation of a Human Papillomavirus Type 16 Virion Pseudotype

Using the protocol described in Example 1, a system was developed for generating infectious papillomaviruses in vitro that facilitates the analysis of papillomavirus assembly and infectivity. Cultured hamster BPHE-1 cells harboring autonomously replicating bovine papillomavirus type 1

(BPV1) genomes were infected with defective Semliki Forest Viruses (SFVs) that express the structural proteins of BPV1. When plated on C127 cells, extracts from cells expressing L1 and L2 together induced numerous transformed foci that could be specifically prevented by BPV neutralizing antibodies, demonstrating that BPV infection was responsible for the focal transformation. Extracts from BPHE-1 cells expressing L1 or L2 separately were not infectious. Although SFV-expressed L1 self-assembled into virus-like particles, viral DNA was detected in particles only when L2 was co-expressed with L1, indicating that genome encapsidation requires L2. Expression of human papillomavirus type 16 (HPV16) L1 and L2 together in BPHE-1 cells also yielded infectious virus. These pseudotyped virions were neutralized by antiserum to HPV16 virus-like particles (VLPs) derived from European (114/K) or African (Z-1194) HPV16 variants, but not by antisera to BPV VLPs, to a poorly assembling mutant HPV16 L1 protein, or to VLPs of closely related genital HPV types.

BPV L1 expressed from recombinant SFV in mammalian cells binds L2 and assembles into VLPs. SFV is a simple positive strand RNA virus. The pSFV-1 expression vector contains the gene for the SFV RNA replicase, the inserted gene and a cis acting virion packaging signal. In vitro synthesized RNA from this vector is co-transfected with a helper vector (pHelper-2) RNA that encodes the SFV structural genes. Upon transfection, the replicase is translated and initiates successive rounds of RNA replication and translation, thereby amplifying the viral RNAs. Translation of the helper RNA leads to production of the SFV virion proteins and encapsidation of the expression vector RNA, but not that of the helper, which lacks the packaging signal. Therefore, the high titer virus generated is defective because it does not encode the SFV virion proteins. Upon infection of susceptible cells (e.g., BHK-21 or BPHE-1), the replicase again amplifies the infecting RNA. Amplification of subgenomic RNAs encoding the cloned gene leads to high level expression of the encoded protein.

Defective BPV1 L1 and BPV1 L2 recombinant Semliki Forest Viruses (SFV-BL1 and SFV-BL2) were generated by co-transfecting BHK-21 cells with in vitro transcribed Helper-2 RNA (Life Technologies) (Berglund, P., et al., 1993, BioTechnology 11, 916–920) and a recombinant pSFV-1 RNA encoding the BPV1 L1 or BPV1 L2 gene. BHK-21 cells were infected with the recombinant SFVs and harvested 72 h later. Expression of BPV1 L1 and L2 was demonstrated by Western blot analysis with monoclonal antibody 1H8 (Chemicon) (Cowsert, L. M., et al., 1988, Virology 165, 613–15)) for L1 and rabbit antiserum to a bacterially-produced glutathione-S-transferase-BPV1 L2 fusion protein for L2 (Kirnbauer, R., et al., 1992, Proc. Natl. Acad. Sci. USA 89, 12180–84). Cell fractionation studies demonstrated that at least 80% of both L1 and L2 resided in the nuclear fraction at the time of harvest.

BHK-21 cells were infected for 3 days with either SFV-BL1 alone or SFV-BL2 alone or were co-infected with the two defective viruses. The cells were harvested and VLPs were prepared by centrifugation through a 40% (w/v) sucrose cushion and cesium chloride isopycnic density gradient centrifugation (Kirnbauer, R., et al., 1993, J. Virol. 67, 6929–36). A visible band with a density of approximately 1.28 g/cm$^3$ was extracted from cesium chloride density gradients of the SFV-BL1 alone and SFV-BL1 plus SFV-BL2 infected cell extract and dialysed into PBS containing 0.5 M NaCl. A corresponding band was not detected in the gradient containing the extract from the cells infected with only the SFV-BL2. Transmission electron microscopy of the BPV1 L1 alone and the L1 plus L2 preparations demonstrated large numbers of 55 nm diameter particles with a morphology similar to BPV virions that were absent from the L2 alone preparation. Analysis of the L1 and L1 plus L2 preparations on a 10% Coomassie stained SDS-PAGE gel revealed a single 55 kDa protein band corresponding to L1. Full length (~70 kDa) L2 was detected by Western blot analysis with rabbit antiserum to bacterially expressed glutathione-S-transferase-BPV1 L2 fusion protein in the L1 plus L2, but not the L1 alone, preparation. Co-immunoprecipitation and co-purification of L1 and L2 showed that L2 co-assembled with L1 into VLPs.

Infectious BPV1 virions are generated by co-expression of both BPV1 L1 and L2 in BPHE-1 cells. Since expression of the recombinant SFVs led to efficient assembly of VLPs in mammalian cells, generation of infectious BPV in vitro and determination of which capsid proteins were required for virion formation was attempted. To this end, the SFV recombinants were used to infect a hamster cell line, BPHE-1, that maintains 50–200 copies of episomal BPV1 genomes per cell (Zhang, Y.-L., et al., 1987, J. Virol. 61, 2924–2928). The BPHE-1 cells were infected with either SFV-BL1 alone or SFV-BL2 alone or co-infected with the two recombinant viruses. The cells were maintained for 30 h, harvested and lysed by sonication, and the extracts were incubated in the medium of monolayers of mouse C127 fibroblasts for 1 h at 37° C. The cells were washed and maintained for 3 weeks in complete medium and stained, and the foci were counted (Dvoretzky, I., et al., 1980, Virology 103, 369–375). Approximately 50 foci occurred in plates of C127 cells treated with BPHE-1 extracts expressing both BPV L1 and L2, but no foci were produced by extracts expressing only BPV L1 or only BPV L2 in multiple experiments.

To determine if focal transformation was due to transfer of BPV1 DNA to the mouse C127 cells, six of the foci were ring cloned and expanded for further analysis (Law, M. F., et al., 1981, Proc. Nat. Acad. Sci. USA 78, 2727–2731). A Hirt extract (Hirt, B., 1967, J. Mol. Biol. 26, 365–369) from each of the six clones was separated on a 0.8% agarose gel, Southern blotted and probed with a [$^{32}$P]-labeled fragment of the BPV genome. High copy number episomal BPV genomic DNA was detected in the extracts of all six clones.

It is possible that the BPV DNA was transferred to the C127 cells by transfection rather than infection by in vitro generated virions. Since neutralizing antibodies should not inhibit transfection, extracts from the L1 and L2 co-expressing BPHE-1 cells were incubated for 1 h at 4° C. in the presence of a 1:100 dilution (10 μl) of rabbit antiserum to either BPV1 or HPV16 L1 VLPs (purified from insect cells) or denatured BPV virions (DAKO) prior to addition to the C127 cells. The L1 plus L2 extract treated with antiserum to BPV VLPs did not produce any foci, whereas extracts treated with antiserum to HPV16 VLPs or denatured BPV virions (which do not neutralize BPV) produced similar numbers of foci as the untreated extract. Treatment of the same extract with monoclonal antibody 5B6 that neutralizes BPV (Roden, R. B. S., et al., 1994, J. Virol. 68, 7570–74), but not a control monoclonal antibody (PAb 101) of the same IgG subtype, also inhibited focus formation. The conformationally-dependent and type-specific neutralization of focal transforming activity demonstrates that infection by BPV virions and not transfection of BPV DNA was responsible for the transformation of the C127 cells.

L2 is required for efficient encapsidation of the BPV genome. L1 assembles into VLPs when expressed in eukaryotic cells, but the function of L2 in generating infectious virus is less clear (Kirnbauer, R., et al., 1992, Proc. Natl.

Acad. Sci. USA 89, 12180–84). L2 may be necessary for some step during the infectious process and/or is necessary for encapsidation of the genome (Zhou, J., et al., 1993, J. Gen. Virol. 74, 763–68). To explore the latter possibility further, ten 500 cm$^2$ plates of BPHE-1 cells were infected with SFV-L1 alone or SFV-L2 alone or were co-infected with SFV-L1 and SFV-L2. The cells were harvested 30 h post infection, sonicated and treated with DNAseI (2000 U) for 1 h at 37° C., and particles were purified. The cesium chloride gradients were fractionated, and the density of each fraction measured. Nucleic acid was purified from 200 μl of each fraction, and BPV DNA was detected by Southern blot analysis. 0.1 ng of BPV-pML plasmid DNA was run as a size standard for uncut, DNAseI-resistant BPV genomes (Sarver, N., et al., 1982, Proc. Natl. Acad. Sci. USA 79, 7147–7151). Only that fraction from the BPHE-1 extracts expressing both L1 and L2 demonstrated significant accumulation of DNAseI-resistant BPV DNA. This fraction had a density (1.31 g/ml) consistent with that of infectious BPV virions obtained from warts under the same conditions (1.32 g/ml).

This fraction was examined by cryo-electron microscopy. Unlike transmission electron microscopy of negatively stained particles, cryo-electron microscopy allows the DNA inside the full capsids to be visualized directly as an electron dense core as opposed to the lower density core of empty particles. Many well formed particles were observed with electron dense cores, as well as a smaller fraction that had a lower density core or were damaged or rod shaped. It was not possible to estimate the number or percentage of full versus empty particles, as the L1 was spread over a large number of fractions as determined by Western blot analysis. However, comparative Southern blot analysis using the cloned BPV genome as a standard indicated that approximately 1 ng of full length DNAseI-resistant DNA was observed in these extracts, which corresponds to approximately $10^8$ DNA molecules. In contrast, only $10^4$ infectious units were isolated from this preparation, indicating that the particle to infectivity ratio is high, approximately $10^4$. Using the same procedures, the number of infectious units and the amount of DNaseI-resistant BPV genomic DNA present in a BPV virion preparation purified from bovine papillomas were measured. The values for the particle to infectivity (as measured by in vitro transformation of C127 cells) ratio obtained were very similar for BPV virions isolated from warts ($2\times10^4$) or generated in BPHE-1 cells ($1\times10^4$).

Generation and neutralization of infectious HPV16{BPV1} pseudotyped virions. Having demonstrated that co-expression of BPV1 L1 and L2 can result in encapsidation of BPV genomes, the question was asked whether genome encapsidation was type specific. L1 and L2 derived from HPV16 were therefore tested for the ability to encapsidate the BPV genome and thereby generate infectious pseudotyped virions. L1 and L2 derived from a wild type HPV16 isolate (114K) were cloned into SFV vectors and expressed in BPHE-1 cells (Heino, P., et al., 1996, Virology 214, 349–359; Kirnbauer, R., et al., 1993, J. Virol. 67, 6929–36). Expression was confirmed by Western blot analysis using monoclonal antibody CamVir-1 (Pharmingen) for L1 and rabbit antiserum to bacterially expressed glutathione-S-transferase-HPV16 L2 fusion protein for L2. Production of infectious virions was assessed using the C127 focus forming assay, as described above. Expression of the L1 and L2 derived from HPV16 in BPHE-1 cells consistently produced infectious virions, referred to as HPV16{BPV1} virus, although approximately 5 to 10-fold less efficiently than BPV L1 and L2. No foci were observed when BPV L1 and HPV16 L2 or HPV16 L1 and BPV L2 were coexpressed, but low-efficiency encapsidation by heterologous pairs of capsid proteins cannot be discounted. Expression in BPHE-1 cells of L1 and L2 derived from a capsid-assembly deficient mutant of HPV16 did not produce any foci (Kirnbauer, R., et al., 1993, J. Virol. 67, 6929–36; Seedorf, K., et al., 1985, Virology 145, 181–185).

Type-specific neutralization of pseudotyped virions. Treatment of the HPV16{BPV1} extracts with 5 or 50 μl of rabbit antiserum to 114K HPV16 VLPs prevented focus formation, whereas addition of antiserum to BPV1 VLPs, denatured BPV virions, or assembly deficient HPV16 L1 of the prototype strain did not prevent focus formation. Both antiserum to HPV16 L1 alone and antiserum to L1/L2 VLPs were neutralizing. Antiserum generated to the L1 VLPs of a divergent Zairian isolate of HPV16 also neutralized the HPV16{BPV1} virions (Cheng, G., et al., 1995, J. Infect. Dis. 172, 1584–1587). This finding demonstrates that infectious virus with HPV16 capsids, not BPV capsids, were produced and that infection of the C127 cells and not transfection by the BPV DNA had occurred.

The ability of antisera raised against VLPs derived from low risk HPV 6b or 11 and high risk HPV18, 31, 33, or 45 to prevent infection by HPV16{BPV1} virions was also tested. All of these sera contain high titers of antibodies ($\geq 10^4$, described in Roden, B. B. S., et al., 1996, J. Virol. 70, 3298–3301) that recognize their corresponding VLPs in ELISA and hemagglutination inhibition assays. However, none of the sera were able to prevent infection of the HPV16{BPV1} virions when 50 μl (or 5 μl) was added to the pseudovirion extract.

Discussion. Despite some progress, difficulties in generating infectious papillomavirus virions in vitro and manipulating them genetically continue to limit studies of this tumor virus (Hagensee, M., and Galloway, D., 1993, Papillomavirus Report 4, 121–124). Use of a mouse xenograft system has led to the limited production of HPV11 and an in vivo infectivity assay (Christensen, N. D., and Kreider, J. W., 1990, J. Virol. 64, 3151–3156; Kreider, J. W., et al., 1987, J. Virol. 61, 590–93). As an alternative approach, raft cultures of human keratinocytes can undergo relatively normal terminal differentiation, thereby permitting expression of the late proteins and virion biosynthesis (Dollard, S. C., et al., 1992, Genes Dev. 6, 1131–42; Meyers, C., et al., 1992, Science 257, 971–73). Small quantities of morphologically correct HPV31b virions have been produced by this method, but no quantitative infectivity assay has been developed using this system (Meyers, C., et al., 1992, Science 257, 971–73). Furthermore, neither the xenografts nor raft cultures are readily amenable to genetic manipulation.

Using recombinant vaccinia virus as a vector for BPV1 L1 and L2, Zhou and colleagues have previously concluded that both L1 and L2 were necessary to encapsidate viral DNA and to generate infectious BPV virions (Zhou, J., et al., 1993, J. Gen. Virol. 763–68). Because their BPV preparations contained infectious vaccinia virus, which is cytotoxic for many cell types, including C127, they used transient expression of viral RNA as their marker for infectivity. One notable difference between the results reported in that study and those obtained here was that their infectivity marker was neutralized by antiserum to denatured BPV1 virions (DAKO). In contrast, the present SFV-derived or cattle papilloma-derived virions induced focal transformation that was not inhibited by any of the several lots of this sera that were tested, in agreement with previous reports that DAKO sera or other sera to denatured virions are non-neutralizing. The results of the Zhou et al. study are therefore ambiguous.

As described here, infectious papillomavirus have been produced by expressing the virion capsid proteins in trans, via defective SFV vectors, in cells that contain an intact viral genome. Production of infectious BPV was monitored by a standard, quantitative, in vitro BPV infectivity assay (Dvoretzky, I., et al., 1980, Virology 103, 369–375). BPV induced focal transformation of C127 cells was specifically inhibited by incubating infectious preparations with neutralizing BPV-antisera, which confirmed that the transformation resulted from BPV infection and not from transfection of viral DNA.

This method of virus production provides the opportunity to determine the functions of the virion proteins in virion formation and to generate virions with specific modifications.

The presence of DNAseI-resistant full length BPV DNA in the extracts expressing L1 plus L2, but not either L1 alone or L2 alone, demonstrates that L2 is required for encapsidation of the BPV genome.

The ability of L1 and L2 derived from HPV16 to encapsidate the BPV genome establishes that any viral DNA packaging signal that exists for papillomavirus genomes is conserved between BPV1 and HPV16, and that, because BPV1 and HPV16 are so highly evolutionarily divergent, such a signal is moreover conserved among papillomaviruses.

The apparent inability to generate infectious virus with BPV L1 and HPV16 L2 or HPV16 L1 and BPV L2 implies L2 from widely divergent papillomaviruses prevented the generation of infectious virus, but this result would not be expected to occur for closely related papillomaviruses.

Expression of HPV16 L1 and L2 in cells containing the BPV genome produced infectious pseudotyped virions with HPV16 capsids. They induced typical BPV type foci, and their infectivity was neutralized by HPV16 antisera and not by BPV antisera. Since HPV16 is not more closely related to BPV1 than are other high risk HPV types, it is expected that a strategy similar to the one reported here for HPV16 can be used to generate infectious pseudotypes for other high risk HPVs, and presumably for any papillomavirus. See Example 4.

Although the focal transformation assay requires 2 to 3 weeks, this problem should in principle be circumvented by incorporation of a rapid and easily detectable marker in the BPV genome.

Results from a number of laboratories have indicated that despite their strict host range, papillomaviruses bind to a variety of cell types derived from diverse species (Muller, M., et al., 1995, J. Virol. 69 948–54; Roden, R. B. S., et al., 1994, J. Virol. 68, 7260–66; Volpers, C., et al., 1995, J. Virol. 69, 3258–3264). The ability of HVP16{BPV1} virions to induce focal transformation of C127 cells establishes that C127 cells express the cell surface receptor for HPV16 virions and are competent to perform the subsequent steps of internalization and uncoating that are required for initiating viral infection. The simplest interpretation of these observations is that BPV and HPV16 share a common intracellular pathway of infection as well as a common cell surface receptor.

The in vitro generation of HPV16{BPV1} pseudotyped virus has allowed, for the first time, the development of an antibody neutralization assay for HPV16 and other high risk HPVs, since there is neither a source of infectious HPV16 or other high risk HPVs, nor an easily scored quantitative assay for the genome of HPV16 or other high risk HPVs. Titers of neutralizing antibodies induced by vaccination are the best correlate of protection for most previously developed prophylactic vaccines (Robbins, J. B., et al., 1995, J. Infect. Dis. 171, 1387–98), as also seems true for the animal papillomavirus protection studies (Breitburd, F., et al., 1995, J Virol. 69, 3959–63, Suzich, J. A., et al., 1995, Proc. Natl. Acad. Sci. USA 92, 11553–11557). It is therefore important to investigate whether the HPV16 VLPs induce high titers of neutralizing antibodies and to determine the degree of cross-protection between various genital HPV types. Until now, it has been necessary to rely on surrogate assays for neutralization, such as ELISA and hemagglutination inhibition (Roden, R. B. S., et al., 1995, J. Virol. 69, 5147–51, Roden, R. B. S., et al., 1996, J. Virol. 70, 3298–3301, Rose, R. C., et al., 1994, J. Gen. Virol. 75, 2445–49). Compared with neutralization, the VLP ELISA is relatively non-stringent because it may recognize non-neutralizing antibodies, while hemagglutination may be overly stringent because a class of neutralizing antibodies (defined for BPV, CRPV and HPV11) does not score in that assay (Roden, R. B. S., et al., 1996, J. Virol. 70, 3298–3301). It is no longer necessary to rely on these surrogate assays for neutralization since presented with the described quantitative in vitro neutralization assay. See Example 5.

The assembly-deficient mutant L1 of the reference HPV16 strain did not induce detectable neutralizing antibodies, reinforcing the concept that most neutralizing epitopes are displayed only on intact particles. The observation that antibodies to a divergent assembly-competent variant (Zaire 1194 (Cheng, G., et al., 1995, J. of Infect. Dis. 172, 1584–1587)), which differs from the 114/K HPV16 isolate at seven L1 amino acids, can efficiently neutralize the HPV16{BPV1} virions made with the 114/K isolate further suggests that VLPs of a single HPV16 variant will induce protection against divergent HPV16 variants (Cheng, G., et al., 1995, J. of Infect. Dis. 172, 1584–1587). However, the pseudotyped virions were not neutralized by antiserum to VLPs derived from six genital HPV types or BPV1. This was true even though two of the VLP types tested, HPV31 and HPV33, are among those most closely related to HPV16, with 84% and 81% L1 amino acid sequence identity, respectively. These anti-VLP sera had titers in ELISA and hemagglutination assays based on the homologous VLP type of at least 10,000 (Roden, R. B. S., et al., 1996, J. Virol. 70, 3298–3301); therefore the negative results in the HPV16{BPV1} neutralization assay were not due to a poor antibody response to these VLPs. The data support the concept that HPV16, is a single serotype, distinct from other genotypes.

The finding that antibodies elicited by assembled HPV16 VLPs can efficiently inhibit infection by the HPV16{BPV1} virions supports the potential utility of these VLPs as prophylactic vaccine candidates. To make an informed decision for the components of a multi-valent VLP-based vaccine to prevent genital HPV infection, it will be necessary to evaluate to what extent antibodies generated against one type of HPV VLP will neutralize infection by other types. The data that rabbit antibodies raised against VLPs derived from other genital HPV types did not neutralize HPV16{BPV1} infection suggest that protection obtained by neutralizing antibodies in humans against these genital HPVs will be type specific. The development of pseudotyped virions of other HPV types, along with HPV16{BPV1}, could be used to more broadly examine the question of cross-neutralization in animal studies and in early phases of human vaccine trials.

II. The Papillomavirus Minor Capsid Protein, L2, Induces Localization of the Virion Components and the Viral Transcription/Replication Protein, E2, to POD Nuclear Structures Using the protocol described in Example 2, the subcellular localization of structural and nonstructural bovine papillomavirus (BPV) proteins in cultured cells has been examined by immunofluorescent. staining and confocal microscopy. When expressed separately, L1, the major capsid protein, showed a diffuse nuclear distribution, while the minor capsid protein, L2, was found to localize to punctate nuclear regions identified as PML oncogenic domains (PODs). Coexpression of L1 and L2 induced a relocation of L1 into the PODs, leading to the colocalization of L1 and L2.

The effect of L2 expression on the distribution of the viral DNA genome and the nonstructural viral proteins E1 and E2, which are required for maintenance of the genome and viral DNA synthesis, was examined. The localization of the E1 protein was unaffected by L2 expression. However, the pattern of anti-E2 staining was dramatically altered in L2-expressing cells. Similar to L1, E2 was shifted from a dispersed nuclear locality into the PODs and colocalized with L2. The recruitment of full-length E2 by L2 occurred in the absence of other viral components. Additionally, in BPV-transformed fibroblasts the autonomously replicating BPV genome was found to be coalesced in an adjoining nuclear region in an L2-dependent manner.

L2 has been shown here to be essential for the generation of infectious BPV. The current results provide evidence for a role for L2 in the organization of virion components by recruiting them to a distinct nuclear domain. This L2-dependent colocalization probably serves as a mechanism to promote assembly of papillomaviruses either by increasing the local concentration of virion constituents or by providing the physical architecture necessary for efficient packaging and assembly. The data also establish a role for a nonstructural viral protein, E2, which binds a conserved sequence motif in papillomavirus genomes, in the localization of the viral genome to the PODs.

Subnuclear localization of BPV capsid proteins. BPHE-1 is a hamster fibroblast cell line that is latently infected with multiple copies of autonomously replicating BPV genomes and expresses the nonstructural viral proteins (Zhang, Y. L., et al., 1987, J. Virol. 61, 2924–2928). The SFV expression system was used to introduce the L2 minor capsid protein into BPHE-1 cells and localize the L2 protein by immunofluorescent staining and laser scanning confocal microscopy. The typical distribution of L2 6 hours after SFV infection indicates the protein was displayed in a distinct intranuclear punctate pattern.

To rule out the possibility that this distribution depended upon the BPV components in the BPHE-1 cells, L2 was expressed, via the SFV vector, in cells that did not harbor papillomavirus sequences. A similar punctate nuclear pattern of L2 staining was also observed in these other cells types, including COS-7, BHK-21 and the human fibroblast cell line 1634. Therefore, this distinct L2 localization is dependent only upon cellular factors and appears to be independent of cell lineage. To determine if this localization was a common feature of papillomavirus L2, the distribution of the human papillomavirus, 16 (HPV16) L2 protein, expressed via an SFV vector, was also examined in these cell lines. The pattern with HPV16 L2 protein was similar to that seen with BPV L2, establishing that this localization is characteristic of papillomavirus L2.

L2-containing punctate structures are PODs. To identify the nuclear domains in which the BPV L2 protein localized, double staining experiments against a number of described nuclear proteins and L2 were performed. No colocalization of the L2 protein was found with coiled bodies, the retinoblastoma protein, p53 or the splicing factor SC35. Although the staining pattern seen with the anti-SC35 antibody was similar to that seen with the anti-L2 antibody, it was evident from the merged image that these regions were exclusive. However, when the distribution of the L2 protein was compared with that of anti-promyelocytic leukemia (PML) protein staining, a nearly complete overlap in protein distribution was observed.

The PML protein is a putative growth suppressor gene product that localizes in subnuclear organelles termed PODs (Chang, K. S., et al., 1995, Blood 85, 3646–3653; Dyck, J. A., et al., 1994, Cell 76, 333–43). The PML distribution appeared to be unaffected by the expression of the L2 protein, and the localization of L2 in the PODs was unrelated to the level of L2 in the cell. This was observed no matter whether the cells were expressing high, intermediate or low levels of L2. All the cells expressing L2 showed a similar punctate distribution, in which L2 colocalized with PML in every cell. Therefore, it is unlikely that this colocalization is an artifact of overexpression.

L2 redirects L1 to PODs. As L1 and L2 coassemble into capsids, the question was asked whether L1 might display a nuclear staining pattern similar to L2. However, when L1 was expressed in BPHE-1 cells, the distribution of L1 protein differed markedly. L1 was present in a nuclear pattern that varied from a diffuse to slightly speckled arrangement with nucleolar exclusion.

This result led to the exploration of the possibility that the subcellular distribution of L1 protein might be affected by coexpression of L2. Therefore, BPHE-1 cells were coinfected with recombinant L1 SFV and recombinant L2 SFV, which are the conditions that lead to the formation of infectious BPV in BPHE-1 cells. The L1 staining pattern was dramatically altered from the diffuse nuclear pattern seen after L1 SFV infection alone. The L2 staining pattern in the coinfected cells was consistent with the distribution of L2 observed in the absence of L1. The distributions of L1 and L2 overlapped substantially in the merge of the two images. In general, L1 did not appear as tightly coalesced as L2. In some cells L1 was observed mostly surrounding, rather than overlapping, the L2 domain. This variability may be due to differences in the kinetics of the infection of individual cells or may reflect intermediate stages in L1 relocation. The conclusion can be drawn that L2 induced the redirection of a substantial proportion of L1 to PODs.

L2 induces colocalization of E2. Next examined was the effect of the expression of the BPV capsid proteins on the distribution of the nonstructural viral protein E2, which is involved in viral genome replication and viral transcription (Chiang, C. M., et al., 1992, Proc. Natl. Acad. Sci. USA. 89, 5799–5803; Spalholz, B. A., et al., 1985, Cell 42, 183–191; Ustav, M., and Stenlund, A., 1991; EMBO J. 10, 449–457). In BPHE-1 cells, E2 was detected as a nuclear protein with a diffuse distribution. There was no apparent effect on the localization of this protein when the L1capsid protein was expressed in these cells. In contrast, L2 expression shifted E2 into punctate regions similar to those observed with the anti-L2 staining pattern. Although it did not interfere with determining the localization of E2, the levels of E2 often decreased substantially during recombinant SFV infection, presumably due to the well documented inhibition of host protein synthesis by SFV (Strauss, J. H., and Strauss, E. G., 1994, Micro. Rev. 58, 491–562). This effect is partially due to interference with the Na+K+ transporter by SFV (Carrasco, L., 1977, FEBS Lett. 76, 11–15; Garry, R. F., et al., 1979, Virology 96, 108–120). A decrease in E2 was also observed in control infections with unrelated SFV recombinants. Infection in the presence of 100 mM KCl helped counteract this problem.

To determine if L2 induced the redistribution of the E2 protein into the L2-staining PODs, double staining of the BPHE-1 cells after infection with the L2-SFV was performed. The majority of the cells showed a diffusely distributed nuclear pattern of E2 staining. However, many cells demonstrated a relocation of E2 into a punctate pattern. All of the L2-expressing cells showed solely a punctate pattern of L2 staining. The coincidence of the E2 and L2 staining was striking in the infected cells that maintained detectable levels of E2.

L2 is sufficient to redistribute full-length E2. BPV-transformed cells with autonomously replicating genomes express three forms of the E2 protein: a full-length 48 kD form that functions in genome replication and transcriptional transactivation and two smaller forms which act as repressors of viral transcription (Hubbert, N. L., et al., 1988, Proc. Natl. Acad. Sci. USA. 85, 5864–5868; Lambert, P. F., J. Virol. 63, 3151–3154; McBride, A. A., et al., 1991, J. Biol. Chem. 266, 18411–18414). The antibody used in the immunofluorescent studies recognizes an epitope in the C-terminal DNA binding domain common to all three proteins and would not distinguish among them. Another feature of the BPHE-1 cells is that an unknown proportion of E2 molecules are bound to the viral genome. Therefore, it was unclear whether the L2-dependent redistribution of E2 in the BPHE-1 might depend on the presence of the viral genome in the cells.

To determine if the L2-dependent redistribution of E2 observed in the BPHE-1 cells could occur between L2 and the full length E2 protein, independently of the viral genome, BHK-21 cells (which do not contain the papillomavirus genome) were infected with both the L2-SFV recombinant and a SFV recombinant expressing the full-length E2. Since the RNA for E2 was produced entirely by the SFV RNA-dependent polymerase in the cytoplasm, production of the alternative E2 mRNAs was precluded. As expected, only the 48 kD form was detected on Western blots of SFV-E2 infected cell extracts. As noted earlier, the L2 distribution in BHK-21 cells was similar to that observed with the BPHE-1 cells. When E2 was expressed in BHK-21 cells, in the absence of L2, the majority of the protein was present in a diffuse nuclear distribution. When the cells were coinfected with L2 and E2, the L2 pattern was unaltered, but the E2 assumed the punctate staining pattern of L2 in the cells that coexpressed the two proteins. These results indicate that L2-dependent localization of the full-length E2 to PODs is independent of the viral genome and viral gene products other than L2.

L2 does not induce the redistribution of E1. The localization of E1 was examined, which participates in viral DNA replication and so is presumably expressed in BPHE-1 cells. The immunostaining with an anti-E1 antibody in BPHE-1 cells was weak. This result was expected, as only low levels of E1 expression from steady state autonomously replicating BPV genomes have been reported (Sun, S., et al., 1990, J. Virol. 64, 5093–5105). No change in the speckled staining pattern was observed after SFV-mediated expression of either capsid protein. Because the intensity of the staining was so low, and the parental line of BPHE-1 was not available as a control, no firm conclusions could be drawn from the E1 analysis in these cells.

To overcome these problems, BHK-21 cells were infected with an E1 recombinant SFV, which resulted in clear immunostaining in a speckled nuclear pattern, while uninfected cells were negative. Coinfection with the L2 and E1 recombinant SFVs resulted in the typical punctate L2 staining pattern, but this expression did not alter the E1 pattern in the coinfected cells. Therefore, the L2 protein does not directly induce a redistribution of E1. However, these results do not preclude the possibility that E1 may localize to PODs indirectly through its well documented interaction with E2 and the viral genome (see below) (Mohr, I. J., 1990, Science 250, 1694–99, Wilson, V. G., and Ludes-Meyer, J., 1991, J. Virol. 65, 5314–5322).

Distribution of the viral genome is altered by L2 expression. It has been estimated that each BPHE-1 nucleus contains 50–200 autonomously replicating copies of the BPV genome (Zhang, Y. L., et al., 1987, J. Virol. 61, 2924–2928). To determine if expression of the BPV virion proteins might influence the distribution of the BPV genome, FISH analysis was performed on BPHE-1 cells that were infected with L1 or L2 recombinant SFV. A fluorescein-labeled PCR probe was generated to the upstream regulatory region of the genome and hybridized in situ after DNA denaturation. Only faint diffuse fluorescent speckles were detected when the genome distribution was examined in cells that were uninfected or infected with L1-SFV. However, in some cells that expressed the L2 protein, the fluorescent probe bound more discrete, coalesced areas. The fluorescent signal could be removed by pretreatment of the cells with DNase, but was unaffected by RNase treatment.

When the location of the genome was compared to that of the L2-POD structures, the DNA was found to be situated adjacent to these domains. Anti-L2 staining performed after FISH revealed that the hybridization and washing procedures resulted in less intense protein detection than seen previously. Nevertheless, the characteristic punctate pattern of L2 was still seen. The cells that were uninfected showed diffuse, barely detectable fluorescence. However, in the cells that expressed high levels of L2, the fluorescent probe bound strongly in about 10–12 spots within the nucleus. In the merged images, it was apparent that the BPV DNA and the L2 protein were located in adjoining domains. This hybridization pattern was not detected in cells that did not express L2. However, this distribution was apparent in only 20–25% of the L2-expressing cells. This variation may be due to differences in the copy number of the infected cells, timing of the particular infection or cell cycle variability, but does not detract from the conclusion about L2 inducing localization of virion components and viral proteins to PODs.

Discussion. As described here, the minor capsid protein L2 has been found to possess the intrinsic capacity to localize to PODs in the absence of other viral components. Further, the presence of L2 in PODs is associated with the recruitment of the major capsid protein L1, the nonstructural protein E2, as well as the viral genome. It is therefore attractive to speculate that PODs are the main structure in which papillomaviruses assemble.

PODs are interchromatinic matrix-bound nuclear bodies with average diameters of 0.3 mm to 0.5 mm in most cells. The cellular function(s) of PODs is largely unknown (Ascoli, C., and Maul, G. J., 1991, J. Cell. Biol. 112, 785–795; Grande, M. A., et al., 1996, J. Cell. Biochem. 63, 280–91). They have also been designated Kr bodies or nuclear domain 10 (ND10) based on the average number of bodies per cell, although their number actually varies and may be higher in transformed cells (Ascoli, C., and Maul, G.

J., 1991, J. Cell. Biol. 112, 785–795; Lamond, A. I., and Carmo-Fonseca, M., 1993, Trends in Cell. Biol. 3, 198–204). PODs may be required for normal maturation of myeloid cells, as their fragmentation is often seen in acute promyelocytic leukemia (Dyck, J. A., et al., 1994, Cell 76, 333–43). Disruption of PODs in this leukemia is associated with heterodimer formation between the normal PML protein and a PML-retinoic acid receptor a (PML-RARa) fusion protein that results from a characteristic t(15;17) chromosomal translocation (de The, H., et al., 1990, Nature 347, 558–561; de The, H., et al., 1991, Nature 347, 558–561, Kakizuka, A., et al., 1991, Cell 66, 663–674). In addition to PML, PODs contain at least 6 other proteins. These include the SP100 protein, which was originally identified as an autoantigen in patients with primary biliary cirrhosis, Int-6, the PIC-1 protein, as well as 52 kD (NP52), 55 kD (NDP55), and 65 kD proteins (Ascoli, C., and Maul, G. J., 1991, J. Cell. Biol. 112, 785–795; Boddy, M. N., et al., 1996, Oncogene 13, 971–982; Desbois, C., et al., 1996, Science 273, 951–53; Epstein, A. L., 1984, J. Virol. 50, 372–379; Szostecki, D., et al., 1990, J. Immunol. 145, 4338–4347).

Some associations have been reported between PODs and the replication of other DNA viruses. Productive viral replication appears to commence in association with PODs for-herpes simplex virus 1 (HSV-1), adenovirus 5 (Ad-5), and simian virus 40 (SV40) (Carvalho, T., et al., 1995, J. Cell. Biol. 131, 45–56; Doucas, V., et al., 1996, Gene Dev. 10, 196–207; Everett, R. D., and Maul, G. G., 1994, EMBO J. 13, 5062–69; Jiang, W. O., et al., 1996, Exp. Cell. Res. 229, 289–300; Maul, G. G., et al., 1996, Virology 217, 67–75; Puvion-Dutilleul, F., 1995, Exp. Cell. Res. 218 9–16). Despite the remarkable convergence to this structure for these three genetically unrelated viruses, the role that this localization plays in the virus-cell interaction has remained unclear.

A number of potential roles in viral replication have been suggested for the association of viral components with PODs. It has been proposed that POD association may be a cellular mechanism that has evolved to limit initial virus replication (Ishov, A. M., and Maul, G. G., 1996, J. Cell. Biol. 134:815–826). The fact that Ad-5 E4-ORF3 and HSV-1 ICPO encode proteins that disrupt PODs as infection proceeds has been taken as evidence supporting this possibility (Doucas, V., et al., 1996, Genes Dev. 10, 196–207; Everett, R. D., and Maul, G. G., 1994, EMBO J. 13, 5062–69; Maul, G. G., et al., 1996, Virology 217, 67–75; Puvion-Dutilleul, F., 1995, Exp. Cell. Res. 218, 9–16). Also, the observation that interferon upregulates the expression of POD proteins is consistent with PODs acting as an antiviral defense mechanism (Chelbi-Alix, M. K., et al., 1995, Leukemia 9, 2027–2033; Grotzinger, T., et al., 1996, Mol. Cell. Biology 16, 1150–56; Lavau, C., et al., 1995, Oncogene 11, 871–876).

Alternatively, POD association may possibly play a positive role in viral replication. This localization might: 1) increase local concentration of viral products and so promote assembly, 2) interfere with normal differentiation and/or apoptotic responses to the viruses in the epithelial cells that are their usual sites of initial replication, 3) facilitate access to cellular transcription and/or replication factors (although there is little evidence that PODs possess these functions), 4) promote essential processing of viral products. In the latter regard, it is interesting that a ubiquitin-dependent protease has recently been shown to be POD associated (Boddy, M. N., et al., 1996, Oncogene 13, 971–982). The findings reported here that the conversion from latent to productive papillomavirus infection in the in vitro system is associated with a redistribution of the relevant viral products to PODs lend strong support to the view that PODs play a positive role in the replication of papillomaviruses.

While studies of Ad-5, HSV, SV40 and Epstein-Barr virus (EBV) have identified products of early genes that interact with, and in some cases disassemble, PODs, they have not determined which gene(s) is responsible for POD localization of the virion components (Doucas, V., et al., 1996, Genes Dev. 10, 196–207; Everett, R. D., and Maul, G. G., 1994, EMBO J. 13, 5062–69; Jiang, W. O., et al., 1996, Exp. Cell. Res. 229, 289–300; Maul, G. G., et al., 1996, Virology 217, 67–75; Puvion-Outilleul, F., 1995, Exp. Cell. Res. 218, 9–16). In this study it was demonstrated that the association of the various papillomavirus components with PODs during productive infection depends upon the L2 minor capsid protein. In the absence of L2, which is essential for the generation of infectious virus, the other viral components display indistinct, heterogeneous distributions. The results indicate that L2 may function to facilitate virion production by inducing the colocalization of the other components required for virion assembly. The recruitment to PODs is likely to represent an important feature that distinguishes productive from latent papillomavirus infection. It is possible that the POD-binding proteins HSV-1 ICPO and EBV EBNA-5, which have been implicated in the escape from latency, may serve an analogous function for their respective viruses.

The results of this study suggest the following model for the productive phase of the papillomavirus life cycle (FIG. 1). The productive cycle begins when L1 and L2 expression is induced by differentiation specific signals in the infected epithelial cells (Dollard, S. C., et al., 1992, Genes Dev. 6, 1131–42; Meyers, C., et al., 1992, Science 257, 971–73). SFV-mediated expression of these two genes substitutes for this induced expression in the present system and demonstrates that differentiation per se is not required for virus production. Virus assembly appears to be triggered by the association of L2 with PODs and the colocalization of L1. It is likely that L1 association with the PODs is the result of a direct interaction of L1 with L2, as stable L1/L2 complexes form in both fully assembled VLPs in vivo and also in partially assembled viral capsid structures, including L1 pentamers, in vitro. Although L1 can self-assemble into VLPs in the absence of L2 (Kirnbauer, R., et al., 1992, Proc. Natl. Acad. Sci. USA. 89, 12180–84; Kirnbauer, R., et al., 1993, J. Viral. 67, 6929–36), L2 increases VLP production 4-fold in insect cells and 100 fold in mammalian cells (Hagensee, M. E., et al., 1993, J. Virol. 67, 315–22; Kirnbauer, R., et al., 1993, J. Viral. 67, 6929–36; Zhou, J., et al., 1993, J. Gen. Viral. 74, 763–68). This greater efficiency could be the result of an increased rate of capsid assembly as a consequence of the L2-mediated concentration of L1 at the PODs.

In some cells containing L2, it appeared that the L1 protein was predominately located around the perimeter of the L2 domains rather than overlapping them. These variations may reflect temporal differences in the SFV infection of individual cells, since all infections appeared to show a mixture of the two patterns. It is likely that a variety of L1 assembly states was detected with the anti-L1 antibody employed here. In vitro, the antibody recognizes pentameric L1 as well as intact virions. It is possible that the L1 detected around the POD perimeter is due to mature virions that have been released from the sites of assembly and show a diminished reactivity with the anti-L2 antibody. Alternatively, the peripheral anti-L1 staining could be due to L1 pentamers in the process of assembling with L2.

L2 also induced the redistribution of E2. The experiments in the BHK-21 cells clearly demonstrated that E2 association with the PODs is L2 dependent, but is independent of L1, other early papillomavirus gene products, or the viral genome. However, there is no evidence that E2 interacts directly with L2. Despite considerable efforts, including coimmunoprecipitation experiments and cosedimentation in sucrose gradients, soluble E2-L2 complexes have not been detected in vivo or in vitro. At present, it has not been feasible to distinguish between the possibilities that the L2 and E2 bind with relatively low affinity, that E2 binds to a component of the PODs that has been altered by L2, or that E2, L2 and a POD component form a trimolecular complex.

It has been unclear how papillomaviruses preferentially package their genomes over cellular DNA, as neither the individual capsid proteins nor the assembled VLPs bind the genome in a sequence specific manner (Mallon, R. G., et al., 1987, J. Viral. 61, 1655–1660; Zhou, J., et al., 1994, J. Viral. 68, 619–25). The present findings on the distribution of the viral genome may have important implications for understanding this process. In latently infected cells, the viral DNA displayed a dispersed distribution. In contrast, the present analysis localized the viral DNA to the PODs in at least some of the cells in the cultures capable of producing infectious virions, suggesting the preferential packaging of the viral genome into virions may result, at least in part, from this directed localization.

Although the mechanism for this relocalization of the viral genome has not been experimentally tested, one can speculate that it is dependent upon the translocation of E2 to the PODs, as E2 avidly binds multiple sites on the viral genome (Androphy, A. J., et al., 1987, Nature 325, 70–73; Li, R., et al., 1989, Genes Dev. 3, 510–526). Since it has not been possible to detect E2 in infectious BPV virions extracted from cattle warts, E2 is visualized as acting catalytically in the process of virion assembly. SV40 T antigen, which is a nonstructural protein of that virus, may be functionally analogous to E2 in this regard. T antigen is a viral genome binding transcription/replication factor that associates with PODs, but does not cause their disruption (Jiang, W. O., et al., 1996, Exp. Cell. Res. 229, 289–300). A signal on the SV40 viral genome that is required for its packaging into virions has been mapped to a segment on the viral DNA that includes the T antigen binding sites (Oppenheim, A., 1992, J. Virol. 66,5320–5328).

III. In Vitro Generation of Infectious BPV Virions in Insect Cells

Using the protocol described in Example 3, infectious BPV has been obtained in Sf9 insect cells by transfecting the cells with full-length circular BPV DNA and infecting them with baculoviruses expressing various combinations of BPV proteins.

Production of infectious BPV, requires E2. When Sf9 cells transfected with the BPV genome were infected with baculoviruses expressing L1 alone, L2 alone, or L1 and L2 together and the extracts were tested in C127 cells, no focal transformation was obtained. However, typical BPV foci were obtained on C127 cells when extracts from BPV DNA transfected Sf9 cells infected with baculoviruses expressing L1+L2 and E2 were examined. The addition of a further baculovirus, which expressed E1, in addition to L1+L2 and E2 baculoviruses, actually resulted in extracts that induced fewer foci on C127 cells, and infection with baculoviruses expressing L1+L2 and E1 did not yield focus forming activity on C127 cells. In addition, focal transformation on C127 cells was not obtained if cells infected with L1+L2 and E2 baculoviruses had been transfected with the BPVpML plasmid (which contains the bacterial pML-2d plasmid inserted within the BPV genome), rather than the isolated religated BPV genome. As with infectious BPV, focal transformation of C127 cells could be prevented if the infectious extract from the L1, L2, and E2 baculovirus infected Sf9 cells was incubated with a neutralizing anti-BPV serum.

Requirement for exogenous E2. The requirement for the E2 baculovirus, in addition to L1 and L2, to obtain infectious virus was different from that of the mammalian cell system. One possible explanation for the difference from the mammalian cell system, which does not require exogenous E2, is that the BPV genes encoding nonstructural viral proteins might not be expressed in the BPV DNA transfected Sf9 insect cells, in contrast to mammalian cells that harbor the BPV genome. To test for this possibility, Sf9 cells transfected with BPV DNA were examined by Western blotting for expression of the BPV E6 protein by probing with a 1:500 dilution of rabbit antiserum to $\lambda$CII BPV E6 fusion protein (Androphy, E. J., et al., 1985, Science 230, 442–445). No E6 expression was detected under these conditions. These results demonstrate that, in contrast to mammalian cells, the BPV genes were not expressed from the transfected BPV genome.

E2 is a viral transcription/replication regulator. The BPV full-length E2 gene encodes a protein that functions as a dimer that binds to sequences present in multiple copies in the upstream regulatory region (URR) of all papillomaviruses (Turek, L., 1994, Adv. Virus Res. 44, 305–356). The E2 protein has been shown to stimulate viral RNA synthesis and viral DNA synthesis. Both of these activities depend upon the binding of E2 to its cognate binding sites (E2BS) in the URR, while viral DNA replication requires the viral E1 gene in addition to E2 protein (Chiang, C.-M., et al., 1992, Proc. Natl. Acad. Sci. USA 89, 5799–5803).

Exogenous E2 does not stimulate BPV transcription. To determine if E2 expression in BPV DNA transfected Sf9 cells might activate expression of other papillomavirus genes required for virion assembly, the presence of the BPV E6 protein (whose expression in mammalian cells is regulated by E2) was sought following infection with the E2 baculovirus. By Western blot analysis, no E6 expression was detected in BPV DNA transfected Sf9 cells expressing E2, whether they were singly infected with the E2 baculovirus or infected with the E2 and L1+L2 baculoviruses. These findings establish that expression of nonstructural viral genes was not activated under these conditions.

Exogenous E2 does not stimulate BPV DNA synthesis. To examine the possibility that the E2 baculovirus might be promoting BPV DNA replication of the input BPV DNA in the transfected Sf9 cells, BPV E1, E2, L1 and L2 were expressed from recombinant baculoviruses separately and in combination in BPV DNA transfected Sf9 cells. After 3 days the cells were harvested, and Hirt extracts prepared (Hirt, B., 1967, J. Mol. Biol. 26, 365–369). The development of resistance to digestion by Dpn I was used to assay for BPV DNA replication in the Sf9 cells. The extrachromosomal DNA was digested with excess Dpn I, separated on a 1% agarose gel, and Southern blotted. The presence of BPV DNA was detected with a [$^{32}$P]-labeled probe generated by random priming from the Spe I-Kpn I fragment of BPV DNA. No evidence of Dpn I resistant BPV DNA was observed (to a sensitivity of 1 ng of DNA per sample). These results indicate that viral replication had not occurred in the insect cells in the presence of E1, or E2, or both proteins. Therefore E2 is not required in BPV DNA transfected Sf9 cells to replicate the BPV genome for packaging.

Exogenous E2 does not increase the amount of BPV L1 or L2. Having ruled out that E2 was stimulating expression of a nonstructural viral gene or fostering the replication of BPV DNA in the Sf9 cells, the question was asked whether E2 expression might be increasing the amount of L1 or L2 to a level critical for virion assembly. To address this possibility, Western blot analysis was used to assess the levels of L1 and L2 in BPV DNA transfected Sf9 cells that had been infected with recombinant baculoviruses expressing L1, L2 and E2 in all combinations and maintained for 3 days. E2 did not increase the level of capsid gene expression; rather, increasing the number of different baculoviruses used for each infection of a plate of BPV-transfected Sf9 cells tended to decrease gene expression from each.

Discussion. In mammalian cells that stably harbor multiple copies of the BPV DNA genome, expression of BPV L1 and L2 via semliki forest virus vectors leads to infectious BPV (neutralizable by BPV antisera). In the same system, expression of HPV16 L1 and L2 via semliki forest virus vectors leads to an infectious pseudotype composed of the BPV genome surrounded by HPV16. L1/L2 capsids (neutralizable by HPV16 antisera). Encapsidation of viral DNA and generation of infectious virus both require expression of L1 and L2, although L1 by itself makes empty capsids.

In insect cells, infectious BPV can be obtained if the BPV DNA genome is introduced into cells, and the cells are infected with baculoviruses expressing an appropriate combination of BPV proteins. It is expected that a similar approach for other papillomaviruses, including HPV, will also produce infectious virus of that-serotype. It is also expected that this approach will be successful for other nonmammalian systems, including yeast, in which expression of structural viral proteins leads to self-assembly of properly folded viral capsids (Sasagawa, T., et al., 1995, Virology 206, 126–35).

The operative finding from the studies carried out in insect cells is that the production of infectious BPV in these cells requires the exogenous production of E2, in addition to the viral genome and the viral structural proteins, L1 and L2. The lack of the requirement for exogenous E2 in mammalian cells is concluded to arise from the fact that E2 is expressed from the episomal BPV genome in mammalian cells, while this is not the case in insect cells. Since BPV is a mammalian virus, it is not surprising that mammalian cells are permissive for expression of nonstructural genes from the viral genome (Turek, L., 1994, Adv. Virus Res. 44, 305–356), while evolutionarily divergent insect cells are nonpermissive for expression of these genes from the viral genome.

The results of experiments conducted in insect cells negate the possibility that exogenous E2, when expressed from recombinant baculovirus, is stimulating BPV DNA synthesis, BPV transcription, or increasing the amount of BPV L1 or L2 protein. It is envisioned that E2 has a different role, which is that of mediating encapsidation of the BPV genome by structural viral proteins. Although the mechanism by which E2 functions to obtain this result is unknown, a model can be postulated. In this model, E2 dimers when bound to their cognate E2 binding sites in the viral genome form a complex that associates with the viral capsid as it is being formed into fully assembled particles. Presumably some aspect of the E2-DNA complex recognizes the assembling viral capsid in a manner that fosters encapsidation of the viral DNA. In this model, E2 might be incorporated into the viral capsid along with the viral genome. Alternatively, encapsidation of the viral DNA might lead to the release of E2, in which case it might be re-used to assist in the encapsidation of other viral DNA genomes. This latter possibility is favored, as the examination of infectious BPV from bovine warts has thus far failed to detect E2 (at a sensitivity of 1 E2 molecule per 10 virions). The key feature of this model is that it provides specificity for genome encapsidation through the well documented high affinity binding of E2, to viral DNA sequences. It is expected that all papillomaviruses encapsidate their genomes via this mechanism. The results showing that L2 can recruit E2 and the viral genome to PODs are consistent with this model. The ability to pseudotype the BPV genome with HPV16 L1 and L2 in mammalian cells establishes that the mechanism of encapsidation is conserved among papillomaviruses. Furthermore, the model, in which a nonstructural DNA binding protein brings viral DNA to the developing virion, may apply to other viruses as well. In most instances, the DNA binding protein (or RNA binding protein for RNA viruses) will be virally encoded. However, there could be viruses in which the DNA binding protein is cell encoded. See Example 6.

Based on the general features of this model, encapsidation of a DNA by papillomavirus machinery requires that the DNA contain the E2BS. This means that. any DNA sequence, such as a gene and a preferred regulatory element, can be encapsidated as a papillomavirus pseudotype so long as it contains the E2BS. Determination of the rules regarding the number and location of E2BS; and whether the E2BS-containing DNA must also be episomal, circular, and approximately 8 kb, is empirical. It is also expected to be possible to eliminate virtually all the viral genes from the DNA and still have the E2BS-containing DNA efficiently pseudotyped by papillomavirus capsid proteins. The finding that HPV16 L1 and L2 can pseudotype the BPV genome shows that E2 can function with heterologous capsids. This means that making a new viral pseudotype does not require using the homologous E2. Instead, the requirements are for the E2 DNA binding protein and its cognate DNA binding site incorporated into a papillomavirus vector DNA, with papillomavirus capsids that can be heterologous in relation to E2. To the extent that the mechanism may apply to other viruses, it can also be extended to them.

Papillomavirus pseudotypes can be made in mammalian cells (Section I). Given the success in making infectious BPV in insect cells (Section III), it is expected additionally to be possible to make papillomavirus pseudotypes in insect cells, providing the cells express E2, L1 and L2. Since L1 and L1/L2 virus-like particles have been made in yeast (Sasagawa, T., et al., 1995, Virology 206, 126–35), and E2 has been shown to function as an E2BS-dependent transcription factor here (Lambert, P., et al., 1989, Genes Dev. 3, 38–48; Morrissey, L., et al., 1989, J. Virol. 63, 4422–4425), it is expected therefore to be possible to make papillomavirus pseudotypes in yeast, with the requirements in yeast being similar to those in insect and, presumably, mammalian cells. Addition of a DNA replication origin that functions in yeast or insect cells (papillomaviruses already have a replication origin that functions in mammalian cells) may increase infectious virus production in the homologous system. Moreover, virus-like particles have now been expressed in bacteria (Nardelli-Haefliger et al., Dec. 1–6, 1996, 15 Intl. Papillomavirus Workshop, 290), which finding raises the expectation that papillomavirus pseutotypes carl be made in bacteria that are engineered to operably encode E2, L1 and L2 genes. Taken together, these properties may make it relatively inexpensive to produce papillomavirus pseudotypes.

Additionally, it should be possible to make viral pseudotypes in the test tube, which would avoid using cells. The interaction of E2 with the other viral components, L1, L2, and E2BS-containing DNA, provides the start of an assay to determine the requirements for in vitro packaging of viral DNA. Efficient packaging may also require cellular components or structures, such as those present in PODs, a fact that would be established empirically.

Because papillomavirus pseudotypes should be infectious for a wide variety of cells, they are expected to have broad application in gene transfer.

IV. Use of Infectious Papillomavirus Pseudoviral Particles in Gene Therapy and Gene Immunization Gene transfer in the context of gene therapy and gene immunization is a clinical strategy in which the genetic repertoire of somatic cells is modified for therapeutic or immunogenic purposes. (Crystal, R. G., 1995, Science 270, 404–410; Mulligan, R. C., 1993, Science 260, 926–932). Essentially, gene transfer, in this context, also involves the delivery, to target cells, of an expression cassette made up of one or more genes and the sequences controlling their expression. This can be carried out ex vivo in a procedure in which the cassette is transferred to cells in the laboratory and the modified cells are then administered to the recipient. Alternatively, gene transfer can be done in vivo, in a procedure in which the expression cassette is transferred directly to cells within an individual. In both strategies, the transfer process is usually aided by a vector that delivers the cassette to the cell where it can function appropriately.

The choice of an ex vivo or in vivo strategy and of the vector used to carry the expression cassette is dictated by the clinical target. The vector systems for which data are available from clinical trials (retroviruses, adenoviruses, and plasmid-liposome complexes) transfer expression cassettes through different mechanisms and thus have distinct advantages and disadvantages for different applications.

Replication-deficient, recombinant retrovirus vectors can accommodate up to 9 kb of exogenous information. Retroviruses transfer their genetic information into the genome of the target cell. This is an advantage when treating hereditary and chronic disorders, but it has risks, including the potential for toxicity associated with chronic overexpression or insertional mutagenesis. The use of retrovirus vectors is limited by the sensitivity of the vector to inactivation, by the fact that target cells must proliferate in order to integrate the proviral DNA into the genome, and by production problems associated with recombination, rearrangements, and low titers.

Adenovirus vectors in current use accommodate expression cassettes up to 7.5 kb. Adenovirus vectors are well suited for transfer applications because they can be produced in high titers and they efficiently transfer genes to nonreplicating and replicating cells. The transferred genetic information remains extrachromosomal, thus avoiding the risks of permanently altering the cellular genotype or of insertional mutagenesis. However, adenovirus vectors in current use evoke nonspecific inflammation and antivector immunity. These responses, together with the extrachromosomal position of the expression cassette, limit the duration of expression to periods ranging from weeks to months. Thus adenovirus vectors will have to be readministered periodically to maintain their persistent expression. Although it is unlikely that repeat administration will be risky, it is not known whether antibodies directed against vector capsid proteins will limit the efficacy of repetitive administration of these vectors.

In theory, plasmid-liposome complexes have many advantages as gene transfer vectors, in that they can be used to transfer expression cassettes of essentially unlimited size, cannot replicate or recombine to form an infectious agent, and may evoke fewer inflammatory or immune responses because they lack proteins. The disadvantage of these vectors is that they are inefficient, requiring that thousands of plasmids be presented to the target cell in order to achieve successful gene transfer.

One of the obstacles to successful gene transfer is obtaining the perfect vector. The ideal vector will overcome the hurdles presented by current vectors, including reduction of the risk for insertional mutagenesis in retrovirus vectors, minimization of the amount of immunity and inflammation evoked by the adenovirus vectors, and enhancement of delivery of the gene to the cell for the plasmid-liposome complexes.

The advantage of using a papillomavirus vector in gene therapy and gene immunization is that it has many desireable qualities as a vector, for it reduces the risk for insertional mutagenesis characteristic of retrovirus vectors (by virtue of its distinct life cycle), it minimizes the amount of immunity and inflammation attributable to adenovirus vectors (see below), and it enhances delivery in contrast to the problem intrinsic to plasmid-liposome complexes (based on its being an animal virus).

An attractive feature of papillomavirus vectors is that there are many different serotypes whose neutralizing antibodies cross-react poorly or not at all. Since neutralizing antibodies can interfere with viral infection, the existence of multiple serotypes means that patients who have developed neutralizing antibodies to one papillomavirus serotype would remain susceptible to infection by other viral serotypes. Encapsidation of the same DNA in different capsid types would allow for multiple "boosts" in a gene therapy or gene immunization protocol without progressive loss in effectiveness of delivery. It would be reasonable to change serotypes by switching L1 molecules, but it may also-be necessary to switch L2 molecules as well as L1. Although L1 contains the major neutralizing epitopes, L2 also contains minor neutralizing epitopes. This point may be important in a sequential administration protocol.

The benefit of using animal viruses to obtain increased delivery is offset by the limitation that these viruses must be propagated in mammalian cells. This kind of propagation is expensive and potentially dangerous due to the possibility of contamination with occult viruses that might be infectious and pathogenic for humans. A strength of the papillomavirus vector is that, even though it is an animal virus, it can be propagated in nonmammalian cells, such as insect and yeast cells, thus enjoying the advantages of being an animal virus while avoiding the pitfalls.

The pseudoviral particles of the invention are useful in the context of gene therapy and gene immunization. The papillomavirus vector uses a E2BS-containing DNA as a base, with the viral genes possibly being deleted from the virus. The expression cassette is inserted, and the infectious papillomavirus is produced in a packaging cell line that contains the E2, L1 and L2 sequences that provide the proteins necessary to package the virus. The vector with its expression cassette enters the target cell via a specific receptor, gets internalized into the cytoplasm, and is uncoated to deliver its DNA genome with the expression cassette into the nucleus, where it functions in an epichromosomal fashion to direct the expression of its product. See Example 7.

In some cases, it might be desireable to provide in the papillomavirus vector a gene encoding E1, which is known to be required for stable maintenance of the viral genome as an episome. This addition would tend to prevent integration of the DNA into the host genome. Of course, the size of the expression cassette would have to be correspondingly adjusted.

Examples of genes carried by the expression cassettes are genes that encode expression products, such as proteins, polypeptides, and peptides (that may be modified by glycosylation, phosphorylition, or amidation, etc.) that are useful in gene therapy or gene immunization (see below). Sequences controlling their expression include promoters (for example, RSV or CMV), enhancers, leader peptides, termination and polyadenylation signals, splicing signals, viral replicons, and genes encoding selectable markers.

Gene therapy is understood to be applicable to the treatment of inherited diseases and, also, acquired diseases, ranging from cardiovascular disorders to cancer to AIDS. Examples of cancer are melanoma, renal cell, ovarian, cervical, neuroblastoma, brain, head and neck, lung, liver, breast, colon, prostate, mesothelioma, leukemia, lymphoma, multiple myeloma, and skin. Examples of other diseases amenable to gene therapy include hemoglobinopathies, severe combined immunodeficiency, hemophilias, familial hypercholesterolemia, inherited emphysema, cystic fibrosis, muscular dystrophy, lysosomal storage diseases, Gaucher's disease, purine nucleoside phosphorylase deficiency, alpha-1 antitrypsin deficiency, Fanconi's anemia, Hunter's syndrome, chronic granulomatous disease, rheumatoid arthritis, peripheral vascular disease, Parkinson's disease, diabetes, osteoporosis, chronic wounds, psoriasis, and atopic dermatitis.

As for gene immunization, it is understood to be applicable to raising a desired immune reaction, generating desired antibodies, or eliciting a desired CTL response. It typically results in protection against disease. These diseases include infectious disease, like viral disease (for example, viral influenza), bacterial disease, and parasitic disease.

Examples of genes carried by the pseudoviral particles of the invention are those that encode, without limitation, constituents of hemoglobin, adenosine deaminase, blood clotting factors (e.g., Factor VIII, Factor IX), receptors (for example, LDL receptor, ACh receptor, hormone receptors), purine nucleoside phosphorylase, alpha-1 antitrypsin, ion channels (for example, CFTR), dystrophin, lysosomal enzymes, insulin, calcitonin, hormones, growth factors, cytokines; growth hormone, erythropoietin, parathyroid hormone, TNF, CSF, IGF, MDR, IL-1, IL-2, IL4, interferons, p53; suicide gene products (for example, herpes simplex virus thymidine kinase, cytosine deaminase, vericella thymidine kinase); antibodies and fragments thereof, components of MHC complexes (for example, HLA-B7), and minor histocompatibility antigens; antisense and triple helix agents; oncogenes; tumor suppressor genes; viral antigens, bacterial antigens, parasitic antigens; connective-tissue proteins (e.g., collagen, elastin, and fibronectin) and foreign proteins (for example, lysozyme and BSA).

It is to be understood that the pseudoviral particles of the invention are used in gene transfer by infecting cells. While ex vivo approaches are plausible, in vivo protocols are preferred. Using either scenario, any cells that express the appropriate cell surface receptors by which the particles gain entry are amenable to infection. Papillomavirus pseudovital particle-mediated gene transfer into epithelial cells is particularly useful. Use of a tissue is contemplated as a bioreactor (to produce proteins for systemic release to treat disease), or to treat the tissue itself. Use of the epithelium, particularly the epidermis, is thus envisioned as a bioreactor, or to treat the epithelium, or the epidermis, itself.

The pharmacologically or biologically active compounds of this invention are generally administered to animals, particularly humans.

These active compounds can be processed in accordance with conventional methods of galenic pharmacy to produce medicinal agents for administration to patients, e.g., mammals, including humans.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds. Suitable pharmaceutically acceptable carriers include water, salt solutions, alcohols, vegetable oils, synthetic fatty vehicles, etc. The pharmaceutical preparations can be mixed with auxiliary agents, e.g., lubricants, preservatives, stabilizers, and the like which do not deleteriously react with the active compounds. They can also be combined where desired with other active agents, e.g., vitamins.

For parenteral application, particularly suitable formulations are injectable, sterile solutions, preferably oily or aqueous solutions, as well as suspensions, emulsions, or implants. These formulations are, if desired, mixed with auxiliary agents, e.g., preservatives, stabilizers, buffers or salts for influencing osmotic pressure, etc.

For enteral application, particularly suitable are tablets, dragees, liquids, drops, suppositories, or capsules. A syrup, elixir, or the like can be used where a sweetened vehicle is employed.

For topical application, these are employed as nonsprayable forms, viscous to semi-solid or solid forms comprising a carrier compatible with topical application and having a dynamic viscosity preferably greater than water. Suitable formulations include solutions, suspensions, emulsions, creams, ointments, powders, liniments, salves, aerosols, etc. For topical application, also suitable,are sprayable aerosol preparations where the active ingredient, preferably in combination with a solid or liquid inert carrier material, is packaged in a bottle or in admixture with a pressurized volatile, normally gaseous propellant, e.g., a freon.

These compositions can be administered intravenously, orally, or through the nose or lung. They can also be administered parenterally or subcutaneously. Administration to the epithelium, or the epidermis, can be by bombardment (for example, with a gene gun) or topical application (for example, with a gene cream) which may or may not require exposure of underlying cells by tape stripping or penetration enhancers.

It will be appreciated that the actual preferred amounts of active compound in a specific case will vary according to the specific compound being utilized, the particular compositions formulated, the mode of application, the particular situs, and the organism being treated. Dosages for a given host can be determined using conventional considerations, e.g., by customary comparison of the differential activities of the subject compounds and of a known agent, and, e.g., by means of an appropriate, conventional pharmacological protocol.

The logic underlying the usefulness of papillomavirus vectors in gene transfer is compelling, and put in the context of gene therapy and gene immunization, the impact of this technology for innovative therapies and prophylactics is enormous.

EXAMPLES

Particular aspects of the invention may be more readily understood by reference to the following examples, which are intended to exemplify the invention, without limiting its scope to the particular exemplified embodiments.

Example 1

Reagents. BPHE-1 cells were obtained from A. Lewis (NIH, Bethesda) (Zhang, Y.-L., et al., 1987, J. Virol. 61, 2924–2928). C127 Clone C cells were obtained from W. Vass (NIH, Bethesda), and BHK-21 cells were obtained from the ATCC. All antisera to VLPs (Roden, R. B. S., et al., 1996, J. Virol. 70, 3298–3301) and monoclonal antibodies have been described previously (Cowsert, L. M., et al., 1988, Virology 165, 613–15; Roden, R. B. S., et al., 1994, J. Virol. 68, 7570–74). Unless otherwise stated, all other reagents, including the SFV expression vectors, were from Life Technologies Inc., Gaithersburg.

Generation of recombinant pSFV-1 plasmids. In order to remove an internal Spe I site, BPV L1 was amplified by PCR in two separate reactions from Bam HI-cut and religated BPVpML DNA using oligonucleotides CCGCTGGATC-CCACTATTATATAGCACCATGGCGT-TGTGGCAACAAGGCCAG (SEQ ID NO:1) and CAGT-TGAGACTAGAGAGCCAC (SEQ ID NO:2) for one reaction, and GTGGCTCTCTAGTCTCAACTG (SEQ ID NO:3) and GCGGTGGATCCT-TATTTTTTTTTTTTTTTGCAGGCT-TACTGGAAGTTTTTTGGC (SEQ ID NO:4) for the second. The products were gel purified and mixed, and the full length L1 gene reamplified by using the outside primers. The product (~1.5 kB) was gel purified, digested with Bam HI and cloned into the Bam HI site of pSFV-1 (Liljestrom, P., and Garoff, H., 1991, BioTechnology 9, 1356–1361). The clone was sequenced to confirm the orientation and absence of the Spe I site and amplification errors. BPV L2 was amplified by PCR from Bam HI-cut and religated BPVpML DNA using GCGGTAGATCTAATATGAGTGCAC-GAAAAAGAGTAAAACGTGCCAGT (SEQ ID NO:5) and CCGCTAGATCTAGGGAGATACAGCT-TCTGGCCTTGTTGCCACAACGC (SEQ ID NO:6) for primers. The product (~1.5 kB) was gel purified, digested with BglII, cloned into the Bam HI site of pSFV-1 and sequenced. Wild type (114/K) and capsid assembly deficient mutant (pAT) HPV16 L1 were excised from pEVmod using BglII and subcloned into pSFV-1. HPV16 L2 was subcloned from a pEVmod vector into the Bam HI site of pSFV-1.NruI (which is linearized using Nru I rather than Spe I). All plasmids were purified from *E.coli* HB101 by alkaline lysis and cesium chloride isopynic density centrifugation.

Generation of recombinant SFV stocks. The recombinant pSFV-1 clones and pHelper-2 (Berglund, P., et al., 1993, BioTechnology 11, 916–920) plasmid were linearized using Spe I (or Nru I for pSFV-1.NruI based clones). The DNAs were phenol/chloroform extracted and ethanol precipitated. To generate SFV RNA, 1 $\mu$g of each linearized pSFV-1 clone and 1 $\mu$g of pHelper-2 were resuspended in 100 $\mu$l reactions containing 1 mM ATP, 1 mM CTP, 1 mM UTP, 0.5 mM GTP, 1 mM RNA capping analog m7G(5')ppp(5')G, 5 mM DTT, 100U human placental RNase inhibitor, 75U SP6 RNA polymerase in 1×SP6 reaction buffer. The reaction mixtures were incubated for 1 h at 37° C. and 2.5 $\mu$l was analyzed on a 0.7% agarose gel to assess the integrity of the SFV RNAs. The remaining RNA was diluted in 1 ml OptiMEM medium, mixed with 100 $\mu$l of Lipofectin in 1 ml of OptiMEM and incubated for 15 min at ambient temperature. BHK-21 cells in a T-75 tissue culture flask were washed and covered with 2 ml of OptiMEM. The RNA/Lipofectin mix was added, and the cells were incubated for 4 h at 37° C. The cells were washed once and maintained for 24 h in 13 ml of complete medium (5% fetal calf serum, 10% tryptose phosphate broth, 10 mM Hepes pH 7.4, 1× nonessential amino acids, 100 U/ml penicillin and 100 $\mu$g/ml streptomycin in Glasgow's MEM). The medium was harvested, clarified by centrifugation (1000×g, 10 min), aliquoted and stored at −80° C.

Generation of papillomavirus in BPHE-1 cells. The recombinant SFV stock was rendered infectious by incubation with 0.5 mg/ml chymotrypsin A4 (Boehringer Mannheim) for 30 min on ice and treatment with 0.5 mg/ml aprotinin (Sigma). 4×10$^6$ BPHE-1 cells maintained for 12–20 h in DMEM containing 10% fetal calf serum, 100 U/ml penicillin and 100 $\mu$g/ml streptomycin in a 100 mm tissue culture plate were washed in D-PBS (containing 0.9 mM calcium and 0.5 mM magnesium). The cells were incubated for 2 h at 37° C. with activated recombinant SFV (titrated to give maximum expression levels, but generally 0.5 ml of each high titre stock) diluted to 25 ml in D-PBS. The virus was aspirated, replaced with complete medium and maintained for 30 h. The cells were scraped from the dish into the medium, which was collected and centrifuged (1000×g, 10 min), and the cell pellet was resuspended in 1 ml of D-PBS. The cells were lysed by sonication (10s, 60% power, Fischer model 150 sonic dismembranator with a microtip).

In vitro focal transformation assay. Cell lysates were added to the medium (DMEM containing 10% fetal calf serum and 100 U/ml penicillin and 100 $\mu$g/ml streptomycin) of monolayers of C127 Clone C cells in 60 mm tissue culture plates. The cells were incubated at 37° C. for 1 h, washed and maintained in DMEM containing 10% fetal calf serum for 3 weeks. The cells were stained with 0.5% (w/v) methylene blue, 0.25% (w/v) carbol fuschin. in. methanol, and the number of foci scored (Dvoretzky, I., et al., 1980, Virology 103, 369–375).

Purification of particles from mammalian cells. For preparation of VLPs, BHK-21 cells were maintained for 3 days post infection with recombinant SFV. To generate full virions, BPHE-1 cells were maintained for only 30 h after infection with recombinant SFV. Ten 500 cm$^2$ culture dishes of cells were scraped from the plates into the medium which was centrifuged (1000×g, 10 min, 4° C.) and the cell pellet resuspended in 5 ml ice cold PBS. The cells were lysed by sonication (1 min, 60% power) and treatment with 0.5% NP-40. Extracts were layered over 30 ml 40% (w/v) sucrose in PBS cushion and centrifuged for 150 min at 80,000×g at 4° C. The pellets were resuspended in 12 ml of 27% (w/w) cesium chloride in PBS and centrifuged for 20 h at 275,000×g. The isopynic density gradient was fractionated and the density of each fraction determined using an Abbe3L refractometer (Milton Roy, Rochester, N.Y.) (Kirnbauer, R., et al., 1993, J. Virol. 67, 6929–36).

Southern blot analysis. Cesium chloride gradient samples were mixed with 2.5 volumes of ethanol and stored overnight at −20° C. The samples were centrifuged (16,000×g, 10 min, 4° C); the pellets were washed with 70% ethanol and resuspended in 10 mM Tris, 1 mM EDTA, pH 8 (TE). Each sample was treated with proteinase K, phenol/chloroform extracted, ethanol precipitated and resuspended in TE. Samples were separated on a 0.8% agarose gel, transferred to nylon membrane (Hybond N, Amersham) and UV cross-linked (12 $\mu$J, UV Autocrosslink 1800, Stratagene). BPV DNA was detected using [$^{32}$P]-labeled random primed SpeI-KpnI fragment of BPVpML under high stringency conditions (Sambrook, J., Fritsch, E. F., and Maniatis, T., 1989, *Molecular Cloning, A Laboratory Manual*, 2nd ed., Cold Spring Harbor Laboratory Press, Cold Spring Harbor, N.Y.).

Electron microscopy. Transmission electron microscopy was performed by binding 5 $\mu$l samples to carbon-coated copper grids, staining with 1% (w/v) uranyl acetate and examination using a Philips EM400RT electron microscope at 100 KV. Samples for cryo-electron microscopy were spun for 15 min in an airfuge onto carbon-coated copper grids, frozen in liquid ethane and also examined in a Philips EM400RT electron microscope at 100 KV (Booy, F. P., et al., 1991, Cell 64, 1007–1015).

Example 2

Antibodies. The monoclonal antibody, B201, directed against the BPV E2 protein, and the polyclonal antiserum, 150-1, which recognizes the BPV E1 protein, were provided by Dr. Elliot Androphy (New England Medical Center, Tufts University School of Medicine). The monoclonal antibody, 5B6, which recognizes BPV L1 capsid protein, and the rabbit polyclonal antiserum, 17/28, raised against the full length BPV L2 capsid protein, have been previously described (Roden, R. B. S., et al., 1994, J. Virol. 68, 7570–74). The monoclonal antibody, 6A8, directed against the BPV L2 protein was provided by A. Bennett Jenson (Georgetown University) (Jin, X. W., et al., 1989, J. Gen. Virol. 70, 1133–40). The antibody against SC35 was purchased from Sigma Immunochemicals (St. Louis, Mo.). The anti-PML antibody, 5E10, was generated by R. van Driel (University of Amsterdam) and was a kind gift of Dr. Louis Staudt (NCI, NIH) (Stuurman, N., 1992, J. Cell. Science 101, 773–84). FITC-conjugated goat anti-mouse immunoglobulin G (IgG) and Texas-red conjugated goat antirabbit IgG were purchased from Jackson Immunoresearch (West Grove, Pa.).

Cell lines. BPHE-1 cells, obtained from A. Lewis (NIH, Bethesda), were grown in DMEM supplemented with antibiotics and 10% FCS (Zhang, Y. L., et al., 1987, J. Virol. 61, 2924–2928). BHK-21 cells, obtained from the ATCC, were grown in Glasgow's medium supplemented with 10% tryptose phosphate broth, antibiotics, nonessential amino acids, HEPES and 5% FCS. For microscopic analyses, cells were seeded onto acid-washed #01 coverslips in 24 well plates at a density of $1 \times 10^5$ cells/well and cultured overnight.

Recombinant Semliki Forest virus expression system. The production of recombinant SFV RNAs and replication defective virus expressing the BPV L1 or L2 capsid protein and the SFV infection protocols are as described here. BPV E1 and E2 were cloned into the BamH1 site of pSFV-1 as PCR products amplified from the BPV genome, the primers for E1 being: 5' CCGCTGGATCCGCACCATGGCAAAC-GATAAAGGTAGC (SEQ ID NO:7) and 3' GCGGTG-GATCCGATCTTGCAACTTATCACTAC (SEQ ID NO:8), and the primers for E2 being: 5' CCGCTGGATCCGCAC-CATGGAGACAGCATGCGAACG (SEQ ID NO:9) and 3' GCGGTGGATCCGAAGAAAAGGCAATGGCAGTG (SEQ ID NO:10). Recombinant viruses expressing each gene were generated as described for L1 and L2. For infection of cells, high titer recombinant SFV stock was treated with 500 µg/ml of chymotrypsin A4 on ice for 30 minutes and then aprotinin was added to 500 µg/ml for an additional 10 minutes. The activated virus was diluted in Dulbecco's PBS with calcium and magnesium to 1/100 and added to cells in 24 well plates. After 60 minutes at 37° C., virus-containing medium was removed and replaced with the normal growth medium supplemented with 100 mM KCl for the remainder of the infection to maintain cellular protein expression. Infections were allowed to continue for 5–6 hours prior to cell fixation and immunolocalization. Although SFV infection will induce cell death in 48 hr., the morphology of the infected cells was not visibly altered at this early time point.

Immunofluorescent staining. Cells were washed three times with cold PBS pH 7.4, fixed by 10 min. incubation at room temperature with 1.0% paraformaldehyde diluted in PBS, and washed three times with PBS/200 mM glycine. Cells were then incubated with primary antibody diluted in PBS/0.1% polyoxyethylene 20 cetyl ether (Brij)(Sigma Chemicals, St. Louis, Mo.) and incubated at 4° C. Polyclonal antisera were used at a dilution of 1/1000. Monoclonal antibodies used as hybridoma supernatants were diluted 1/100. Purified antibodies were used at a concentration of 5 µg/ml. For double immunofluorescent staining the primary antibodies were incubated in unison. After incubation, coverslips were washed three times with PBS/0.1% Brij. Secondary antibodies were diluted to 5 µg/ml in PBS/0.1% Brij and incubation was performed at 4° C. After this incubation, cells were washed thoroughly in PBS/0.1% Brij and inverted onto Fluoromount-G mounting solution (Southern Biotechnology Associates, Birmingham, Ala.) on a glass slide. Fluorescence was examined using a BioRad MRC 1024 laser scanning confocal system attached to a Zeiss Axioplan microscope. All images were acquired with a Zeiss 63× N.A. 1.4 planapo objective using the photon counting mode. Control coverslips established that fluorescence in green and red channels was not overlapping and that antibody binding was specific for the intended antigen. Images were collaged and scale-adjusted using the Adobe Photoshop program.

Fluorescent in situ hybridization (FISH). A probe to the upstream regulatory region of the BPV genome (7173–28) was PCR amplified using the 5' oligo, CGGCAGCTTGCAATGTGCTGTGTCAGTTG (SEQ ID NO:11), and the 3' oligo, CGCGAAGCTTAACGGTGATGGTGTGATTAT (SEQ ID NO:12). The HindIII cloning site is in bold and the BPV sequence overlap is underlined. The PCR reactions were performed using a fluorescein labeling mix (Boehringer Mannheim Indianapolis, Ind.) in which fluorescein-labeled dUTP is incorporated into the PCR product. Cells were fixed in 2% paraformaldehyde/PBS with 5 mM MgCl2 for 10 min. at room temperature. After 3 washes in PBS/200 mM glycine, the cells were permeabilized with 0.2% TritonX-100 in PBS (v/v) for 5 min. and rewashed with PBS. Immediately prior to hybridization cells were washed with 2×SSC (1×SSC is 150 mM NaCl and 15 mM sodium citrate) at room temperature.

Labeled probe (150 ng/coverslip) was brought to a final volume of 10 µl with 1×SSC and dried under vacuum. The probe was resuspended in 7 µl of 100% deionized formamide and heated to 90° C. for 5 min. 7 µl of hybridization buffer was added to the probe to give a final concentration of 50% formamide, 2×SSC, 1× Denhardt's solution, 10% dextran sulfate and 50 mM Tris pH 7.5. In rapid succession, this mixture was applied to the coverslip, inverted onto a glass slide, covered with a second glass slide spaced with a 1 mm spacer, sealed with Parafilm (American National Can, Greenwich, Conn.) and incubated for 10 minutes at 90° C. The slides were then transferred to a humid 37° C. chamber overnight. After overnight incubation, the coverslips were washed in several changes of 50% formamide/2×SSC at 37° C. for 60 min., 2×SSC at 37° C. for 30 min. and 2×SSC at room temperature for 30 min.

For experiments in which protein localization was also desired, after the final posthybridization wash, antibody staining was performed as described above except that detergent was not included in the incubations or washes.

Example 3

Generation of BPV genome. To produce the circular BPV DNA, cesium chloride purified BPVpML plasmid DNA, which contains the BPV genome cloned via its unique Bam HI site, was digested with Bam HI, phenol/chloroform extracted, and precipitated. The DNA was resuspended at 500 μg/ml in ligation buffer (50 mM TrisHCl pH7.6, 5 mM MgCl$_2$, 1 mM ATP, 1 mM DTT) containing 0.05 Weiss units/μg of T4 DNA ligase and incubated overnight at 16° C. to promote self-ligation of the BPV genome. The religated DNA was precipitated with ethanol, washed and resuspended overnight in TE (10 mM TrisHCl pH8.0, 1 mM EDTA) at 1 μg/μl.

Generation of baculoviruses expressing BPV late and/or early genes. Baculoviruses (Summers, M. D., and Smith, G. E., 1987, *A manual of methods for baculovirus vectors and insect cell culture procedures. Bulletin No.* 1555, Texas Agricultural Experiment Station, College Station, Tex.) that expressed BPV L1 alone, L2 alone, or L1 plus L2 (L1+L2) together have been described (Kirnbauer, R., et al., 1993, J. Virol. 67, 6929–36). Similar baculoviruses expressing BPV E1(Blitz, I. L. and Laimins, L. A., 1991, J. Virol. 65, 649–656) or E2 (Monini, P., et al., 1993, J. Virol. 67, 5668–5676) were obtained from Elliot Androphy, New England Medical Center, Boston, Mass.

Generation of papillomaviruses in insect cells. Prior to infection, the Sf9 cells were maintained in spinner flasks at 27° C with Grace's medium containing 10% fetal calf serum and 0.01% (v/v) pluronic F-68. Cells were harvested by centrifugation (300×g, for 5 min) and resuspended at $10^6$/ml in serum-free Grace's medium. 3×$10^6$ Sf9 cells were plated per 60 mm tissue culture dish and allowed to adhere for 30 min. For each plate, 15 μg of ligated BPV DNA in 1 ml of serum-free Grace's medium was mixed gently with 35 μl of Lipofectin (Life Technologies) in 1 ml of serum-free Grace's medium in a polystyrene tube and incubated for 30 min at room temperature. The medium in the culture dishes was aspirated and replaced with the DNA/Lipofectin complex in 2 ml of serum free Grace's medium. The cells were incubated for 4 h at 27° C., the medium aspirated, and replaced with 2 ml of serum-free Grace's medium containing 33 μl of the various combinations of L1, L2, E1, and E2 expressing recombinant baculoviruses (M01~10). After a one hour infection, the medium was removed and replaced with 5 ml of Grace's medium containing 10% fetal calf serum, 100 U/ml penicillin G and 100 μ/ml streptomycin. The cells were maintained at 27° C. for 72 h in a humidified atmosphere and harvested by scraping from the plate. The plates were washed once with PBS to remove all remaining cells, and the cells were then collected by centrifugation (300×g, 5 min). The medium was aspirated and the cell pellet stored at −80° C.

In vitro focal transformation assay. To test for the production of infectious BPV, a standard focal transformation assay on C127 cells was carried out (Dvoretzky, I., et al., 1980, Virology 103, 369–375). One milliliter of D-PBS (containing 0.9 mM calcium and 0.5 mM magnesium) was added to each cell pellet and the cells were lysed by 15 sec of sonication on ice (microtip, 60% power, Fisher sonic dismembranater model 150). For neutralization studies, antibody was added at this stage and incubated for 1 h on ice. The cell lysates were mixed into 5 ml of medium (DMEM containing 10% fetal calf serum, 100 U/ml penicillin G, and 100 μg/ml streptomycin maintained at 37° C. in a humidified 5% $CO_2$/95% air atmosphere) over confluent monolayers of low passage number mouse C127 clone C cells in 60 mm culture dishes. After a 1 h incubation at 37° C., the cells were washed once and then 5 ml of fresh medium was added. The following day the medium was replaced with DMEM containing 10% fetal calf serum that was used to maintain the cells for 2–3 weeks, replenishing twice weekly. The foci were stained with methylene blue (Sigma, M9140) and carbol fuchsin (Sigma, C-4165) in methanol and scored.

Example 4

A strategy similar to the one reported here for HPV16 is used to generate infectious pseudotypes for other papillomaviruses. The HPV11 genome is produced by isolating a HPV11 DNA clone. Baculoviruses expressing the E2, L1 and L2 genes of HPV18 are prepared. Sf9 insect cells are transfected with the HPV11 genome and infected with the E2, L1 and L2 expressing baculoviruses. Conditions are provided for generation of HPV18{HPV11} pseudotypes, and the particles are harvested. To test for the production of infectious pseudotypes, cultured mammalian cells are identified that can be infected by HPV18 virions. An in vitro infectivity assay is then carried out using these cells. Although focal transformation may not be the endpoint, infection can be identified by incorporation of a rapidly and easily detectable marker into the papillomavirus genome. To determine whether transformation is due to transfection or infection, neutralization studies are conducted. Neutralizing antibodies are generated against HPV18 virions. The HPV18{HPV11} pseudotypes are preincubated with these antibodies and then administered to cells. If the neutralization step blocks infectivity, then infection and not transfection by the HPV18{HPV11} virions will have occurred.

Example 5

Papillomavirus VLPs are attractive candidates for vaccines against papillomavirus infections because they present conformational virion surface epitopes but lack the potentially oncogenic viral genome. Supporting the vaccine potential of VLPs are the findings that they induce high titers of apparently type-specific neutralizing antibodies against infectious papillomaviruses. In addition, vaccination with VLPs stimulated type-specific, antibody-mediated in vivo protection against high-dose experimental infection by papillomaviruses. As described here, in vitro assays have now been developed that directly measure neutralizing antibodies to high-risk HPVs, e.g., HPV16. This required the in vitro generation of HPV16 virions and the development of a quantitative in vitro assay for infectivity. This assay is used in this protocol, for example, to monitor the generation of neutralizing antibodies in the development of an immunoprophylactic vaccine against papillomavirus infection using papillomavirus VLPs, or in the monitoring of protection for previously developed immunoprophylactic vaccines since titer of neutralizing antibodies are the best correlate of protection. Although the focal transformation assay requires 2 to 3 weeks, this problem is circumvented by incorporation of a rapid and easily detectable marker into the papillomavirus genome. Accordingly, a β-galatosidase expression cassette is substituted for most of a viral genome, such as the BPV genome, leaving only those cis-elements, such as the E2 binding sites, required for efficient encapsidation. In this example, the BPV genomes are encapsidated with HPV16 L1 and L2 structural proteins to produce HPV16{BPV1/β-galactosidase} pseudotyped virions. Protection for immunoprophylactic vaccines against HPV16 infection using HPV16 VLPs is monitored by testing for neutralizing antibodies against HPV16. A sample is obtained from a vaccinee and mixed with HPV16{BPV1/βgalactosidase} pseudotyped virions. Infection of C127 cells with HPV16{BPV1/β-galactosidase}, where infection is indicated by a color change, represents a quantitative in vitro neutralization assay that can be conducted in 3-4 days. Neutralizing antibodies will block infectivity. The presence of neutralizing antibodies can be determined by relating the amount of infectivity measured with the amount of infectivity measured for a control sample known to be free of neutralizing antibodies. The concentration of neutralizing antibodies can be established by relating the amount of infectivity measured with the amount of infectivity measured for samples containing known amounts of neutralizing antibodies. The waning of neutralizing antibodies in a vacinee is used as an indication that a booster inoculation with the HVP16 VLP vaccine is warranted.

Example 6

The following is a laboratory protocol for preparing infectious herpesvirus pseudoviral virions in non-mammalian cells. The herpesvirus genome is produced by isolating a, herpesvirus DNA clone. An expression cassette is prepared operably encoding a cloned-DNA. The expression cassette is substituted for the viral genes, while maintaining the packaging signal, to obtain a herpesvirus vector DNA. Baculoviruses expressing the nonstructural protein(s) for the packaging the viral genome in the empty capsid, and expressing the structural proteins of the herpesvirus capsid are prepared. Sf9 insect cells are transfected with the herpesvirus vector DNA and infected with the nonstructural and structural protein-expressing baculoviruses. Conditions are provided for generation of herpesvirus pseudotypes, and the virions are harvested. To test for the production of infectious virions, cultured mammalian cells are identified that can be infected by wild type virions. An in vitro infectivity assay is then carried out using these cells. Infection is identified by testing for the production of the protein encoded by the cloned DNA. To determine whether transformation is due to transfection or infection, neutralization studies are conducted. Neutralizing antibodies are generated against wild type virions. The herpesvirus pseudotypes are preincubated with these antibodies and then administered to cells. If the neutralization step blocks infectivity, then infection and not transfection by the pseudotyped virions will have occurred. The infectious herpesvirus pseudoviral virions are used to transfer the cloned DNA into mammalian cells of the central nervous system.

Example 7

The following is a clinical protocol for treatment of wrinkles of the face. The HPV1 genome is produced by isolating a HPV1 DNA clone. An expression cassette is prepared operably encoding proelastin, the precursor for elastin, a molecule found in the connective tissue of the skin. The expression cassette is substituted for the viral genes, while maintaining the E2BS, to obtain a HPV1 vector DNA. Baculoviruses expressing the E2, L1 and L2 genes of HPV1 are prepared. Sf9 insect cells are transfected with the HPV1 vector DNA and infected with the E2, L1 and L2 expressing baculoviruses. Conditions are provided for generation of HPV1{HPV1/elastin} pseudotypes, and the particles are harvested. To test for the production of infectious particles, cultured mammalian cells are identified that can be infected by HPV1 virions. An in vitro infectivity assay is then carried out using these cells. Infection is identified by testing for the production of elastin. To determine whether transformation is due to transfection or infection, neutralization studies are conducted. Neutralizing antibodies are generated against HPV1 virions. The HPV1 pseudotypes are preincubated with these antibodies and then administered to cells. If the neutralization step blocks infectivity, then infection and not transfection by the HPV1{HPV1/elastin} virions will have occurred. Infectious HVP1{HPV1/elastin} particles are formulated in a cream. The cream is applied topically to the face of a patient. The particular dose of virus is selected based on clinical trials in which increasing the concentration does not appreciably increase the efficiency of gene transfer and decreasing the concentration results in the efficiency of gene transfer being significantly decreased. About 10 days following the administration of virus, the patient is evaluated for reduction of wrinkles to the face, and the cream is reapplied for another treatment on an as-needed basis.

While particular embodiments of the invention have been described in detail, it will be apparent to those skilled in the art that these embodiments are exemplary, rather than limiting. The true scope of the invention is that defined within the attached claims and equivalents thereof. All references cited herein are hereby expressly incorporated by reference.

What is claimed is:

1. An infectious papillomavirus pseudoviral particle comprising:
   (a) a papillomavirus vector DNA which comprises a papillomavirus E2 binding site and an expression cassette comprising a gene and a sequence controlling expression of said gene; and
   (b) a papillomavirus capsid which comprises L1 and L2 structural proteins, such that said capsid encapsidates said vector DNA, wherein said gene is derived from a first biological species and said L1 structural protein is derived from a second biological species and said first biological species is different from said second biological species.

2. The infectious papillomavirus pseudoviral particle of claim 1, wherein each of said L1 and L2 structural proteins is derived from a human papillomavirus.

3. The infectious papillomavirus pseudoviral particle of claim 1, wherein said gene is a human gene.

4. A method of making infectious papillomavirus pseudoviral particles comprising:
   (a) providing a cell line which expresses a papillomavirus E2 DNA binding protein and L1 and L2 structural proteins;
   (b) transforming said cell line with a papillomavirus vector DNA which comprises a papillomavirus E2 binding site and an expression cassette comprising a gene and a sequence controlling expression of said gene, wherein said papillomavirus E2 binding site is a cognate binding site of said E2 DNA binding protein, and wherein said gene is derived from a first biological species and said L1 structural protein is derived from a second biological species and said first biological species is different from said second biological species;
   (c) providing conditions for the encapsidation of said vector DNA by a capsid which comprises said L1 and L2 structural proteins to generate said particles; and
   (d) harvesting said particles.

5. The method of claim 4, wherein said cell line is a mammalian cell line, an insect cell line, or a yeast cell line.

6. A cell line comprising the infectious papillomavirus pseudoviral particle of claim 1.

7. Infectious papillomavirus pseudoviral particles made by the method of claim 4.

8. A method of transferring a gene into a cultured mammalian cell comprising:
   (a) providing the infectious papillomavirus pseudoviral particle of claim 1, wherein the sequence controlling expression of said gene in said expression cassette is a sequence suitable for gene expression in a cultured mammalian cell; and
   (b) infecting a cultured mammalian cell with said particle of (a) such that said cultured mammalian cell is transformed with said gene.

* * * * *